United States Patent
Robertson et al.

(10) Patent No.: US 6,482,587 B1
(45) Date of Patent: *Nov. 19, 2002

(54) METHODS TO INHIBIT OR ENHANCE THE BINDING OF VIRAL DNA TO GENOMIC HOST DNA

(75) Inventors: Erle S. Robertson, Plymouth; Murray A. Cotter, Ann Arbor, both of MI (US)

(73) Assignee: The Regents of the University of Michigan, Ann Arbor, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/410,399

(22) Filed: Oct. 1, 1999

(51) Int. Cl.$^7$ .................................................. C12Q 1/70
(52) U.S. Cl. .......................... 435/5; 424/9.2; 435/7.21; 435/325; 530/350
(58) Field of Search .............................. 424/9.2; 435/5, 435/7.21, 238, 325; 530/350

(56) References Cited

U.S. PATENT DOCUMENTS 5,831,001 A * 11/1998 Twist et al. .................. 530/328

OTHER PUBLICATIONS

Cearman et al. "In vitro establishment and characterization of two aquired immunodeficiency syndrome—related lymphoma cell line (BC–1 and BC–2) containing Kaposi's sarcoma–associated herpesvirus–like (KSHV) DNA sequences." Blood vol. 86 (1995) p2708–2710.*

Chodosh et al. "Eradication of latent Epstein–Barr virus by hydroxyurea alters the growth–transformed cell phenotype." Journal of Infectious Diseases vol. 177 (1998), p 1194–1201.*

Rainbow et al. "The 222– to 234–kilodalton latent nuclear protein(LNA) of Kaposi's sarcoma–associated herpesvirus (Human herpesvirus 8) is encoded by orf73 and is a component of the latency associated . . . " Journal of Virology vol. 71 (1997), p 1194–1201.*

Makey et al. "Multiple regions within EBNA1 can link DNAs." Journal of Virology vol. 69 (1995), p 6199–6208.*

Petti et al. "Subnuclear localization and phosphorylation of Epstein–Barr virus latent infection nuclear proteins." Virology vol. 176 (1990), p 563–565.*

Horenstein et al. "Epstein–Barr virus latent gene expression in primary effusion lymphomas containing Kaposi's sarcoma–associated herpesvirus/human herpesvirus–8." Blood vol. 90 (1997), p 1186–1191.*

Kim et al. An imperfect correlation between DNA replication activity of Epstein–Barr virus nuclear antigen 1 (EBNA–1) and binding to the nuclear import receptor, Rch/importin alpha. Virology, vol. 239 (1997) p. 239–340.*

Huang et al. A yeast genetic system for selecting small molecule inhibitors of protein–protein interaction of nano-droplets. Proceedings of the National Academy of Science. vol. 94 (1997) p. 13396–13401.*

McNabb et al. Genetic biochemical probes for protein–protein interactions. Current Opinion in Biotechnology. vol. 7 (1996) p. 554–559.*

Roizman R. Herpesviridae. In: Field Virology, third edition. Ed: Fields et al. 1996. Lippencot–Raven Publisher, Philadelphia.*

Martin et al. Sexual transmission and the natural history of human hepesvirus 8 infection. New England Journal of Medicine. vol. 338, No. 14 (1988) p. 948–954.*

Englund J. A. The many faces of Epstein–Barr virus. Postgraduate Medicine. vol. 83, No. 2 (1988) p. 167–180.*

Ballestas et al. Efficient persistence of extrachromosomal KSHV DNA mediated by latency–associated nuclear antigen. Science (Apr. 1999) vol. 284, pp. 641–644.*

Aiyar, A., et al. "The plasmid replicon of EBV consists of multiple cis–acting elements that facilitate DNA synthesis by the cell and a viral maintenance element," *EMBO* 17:63940–6403 (1998).

Ambinder, R.F., et al. "Definition of the sequence requirements for binding of the EBNA–1 protein to its palindromic target sites in Epstein–Barr virus DNA," *J. Virol.* 64:2369–2379 (1990).

Aster, J.C., et al., "Oncogenic forms of NOTCH1 lacking either the primary binding site for RBP–Jkappa or nuclear localization sequences retain the ability to associate with RBP–Jkappa and activate transcription," *J. Biol. Chem.* 272:11336–11343 (1997).

Chang, Y. et al. "Identification of herpesvirus–like DNA sequences in AIDS–associated Kaposi's sarcoma" *Science* 266:1865–1869 (1994).

Chu, B.C. and Orgel, L.E. "Ligation of oligonucleotides to nucleic acids or proteins via disulfide bonds," *Nucl Acid Res* 16:3671–3691 (1988).

Decker, L., et al. "The Kaposi sarcoma–associated herpesvirus (KSHV) is present as an intact latent genome in KS tissue but replicates in the peripheral blood mononuclear cells of KS patients," *J Exp Med* 184:283–288 (1996).

Ganem, D. "KSHV and Kaposi's sarcoma: the end of the beginning of the end?," *Cell* 91:157–160 (1997).

(List continued on next page.)

*Primary Examiner*—Jeffrey Stucker
*Assistant Examiner*—Ulrike Winkler
(74) *Attorney, Agent, or Firm*—Medlen & Carroll, LLP

(57) ABSTRACT

This invention relates to novel reagents and methods for the screening of compounds that may be agonistic or antagonistic to the binding of viral DNA to the chromosomes of host cells, that may be used in gene therapy and that may be used to treat tumor viruses.

3 Claims, 14 Drawing Sheets

(4 of 14 Drawing Sheet(s) Filed in Color)

OTHER PUBLICATIONS

Gao, S.J., et al. "Seroconversion to antibodies against Kaposi's sarcoma–associated herpesvirus–related latent nuclear antigens before the development of Kaposi's sarcoma," *N Engl J Med* 335:223–242 (1996).

Grogan, E.A., et al. "Two Epstein–Barr viral nuclear neoantigens distinguished by gene transfer, serology and chromosome binding," *PNAS* 80:7650–7653 (1983).

Hal Jones, C., et al. "Interaction of the lymphocyte–derived Epstein–Barr virus nuclear antigen EBNA–1 with its DNA–binding sites," *J. Virol.* 63:101–110, (1989).

Harris, A., et al. "Random associations of Epstein–Barr virus genomes with host cell metaphase chromosomes in Burkitt's lymphoma–derived cell lines," *J Virol* 56:328–332 (1985).

Kasahara et al., "Tissue–Specific Targeting of Retroviral Vectors Through Ligand–Receptor Interactions," *Science* 266:1373–1376 (1994).

Kedes, D.H., et al. "Identification of the gene encoding the major latency–associated nuclear antigen of the Kaposi's sarcoma–associated herpesvirus," *J Clin Invest* 100:2606–2610 (1997).

Leonetti, et al., "Antiviral activity of conjugates between poly(L–lsine) and synthetic oligodeoxyribonucleotides," *Gene,* 72:32–33 (1988).

Mackey, D. and Sugden, B. "Studies on the mechanism of DNA linking by Epstein–Barr virus nuclear antigen" *J. Biol. Chem.* 272:29873–29879 (1997).

Matsukura, et al., "Phosphorothioate analogs of oligodeoxynucleotides: Inhibitors of replication and cytopathic effects of human immunodeficiency virus," *Proc. Nat. Acad. Sci.,* 84:7706–10 (1987).

Miller, P., et al., "Nonionic Nucleic Acid Analogues. Synthesis and Characterization of Dideoxyribonucleoside Methylphosphonates," *Biochemistry,* 18:5134–43 (1979).

Miller, P., et al., "Biochemical and Biological Effects of Nonionic Nucleic Acid Methylphosphonates," *Biochemistry* 20:1874–1880 (1981).

Moore, P.S., et al. "Primary characterization of a herpesvirus agent with Kaposi's sarcoma," *J Virol* 70:549–558 (1996).

Neipel, F., et al., "Fleckenstein Cell–homologous genes in the Kaposi's sarcoma–associated rhadinovirus human herpesvirus 8: determinants of its pathogenicity?," *J. Virol* 71:4187–4192 (1997).

Rainbow, L., et al. "The 222– to 234–kilodalton latent nuclear protein (LNA) of Kaposi's sarcoma–associated herpesvirus (human herpes 8) is encoded by orf73 and is a component of the latency–associated nuclear antigen" *J Virol* 71:5915–5921 (1997).

Ramakrishnan, V., et al., "Histone structure and the organization of the nucleosome," *Annu Rev Biophys Biomol Struct* 26:83–112 (1997).

Rawlins, D.R., et al. "Sequence–specific DNA binding of the Epstein–Barr virus nuclear antigen (EBNA–1) to clustered sites in the plasmid maintenance region," *Cell* 42:859–868 (1985).

Renne, R., et al., "The size and conformation of Kaposi's sarcoma–associated herpesvirus (human herpesvirus 8) DNA in infected cells and virions," *J Virol* 70:8151–8154.

Russo, J.et al., "Nucleotide sequence of the Kaposi sarcoma–associated herpesvirus (HHV8)," *PNAS* 93:14862–14867 (1996).

Sambrook et al., "Molecular Cloning: A Laboratory Manual," 2nd ed. (1989) Cold Spring Harbor Laboratory Press, Cold Spring Harbor, N.Y.

Simpson, G.R. et al. "Prevalence of Kaposi's sarcoma associated herpesvirus infection measured by antibodies to recombinant capsid protein and latent immunofluorescence antigen" *Lancet* 348:1133–1138 (1996).

Valsesia–Wittmann et al., "Modifications in the binding domain of avian retrovirus envelope protein to redirect the host range of retroviral vectors," *J. Virol.* 68:4609–4619 (1994).

Wolffe, A.P. "H1" *Intl J Biochem and Cellbio* 29:1463–1466 (1997).

Yates, J.L., et al. "Stable replication of plasmids derived from Epstein–Barr virus in various mammalian cells," *Nature* 313:812–815 (1985).

Zerial, et al., "Selective inhibition of the cytopathic effect of type A influenza viruses by oligodeoxynucleotides covalently linked to an intercalating agent," *Nucleic Acids Res.,* 15:9909–19 (1987).

Ballestas M, et al., "Efficient Persistence of Extrachromosomal KSHV DNA Mediated by Latency–Associated Nuclear Antigen," *Science* 284:641–644 (1999).

Senear DF, et al., "Analysis of protein and DNA–mediated contributions to cooperative assembly of protein–DNA complexes," *Methods* 16(1):877–96 (1998).

Jones, S. et al., "Protein–DNA Interactions: A Structural Analysis," *J. Mol. Biol.* 287:877–896 (1999).

Callahan, J. et al., "Distinct patterns of viral antigen expression in Epstein–Barr virus and Kaposi's sarcoma–associated herpesvirus coinfected body–cavity–based lymphoma cell lines: Potential switches in latent gene expression due to coinfection." *Virology* 262(1): 18–30 (1999).

* cited by examiner

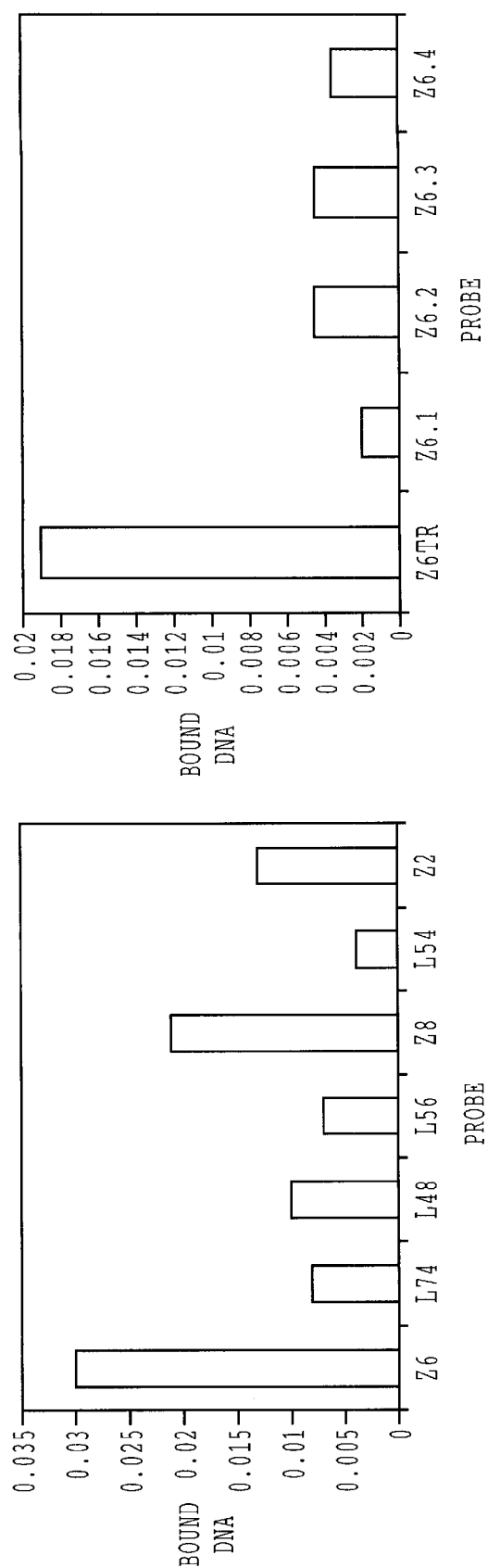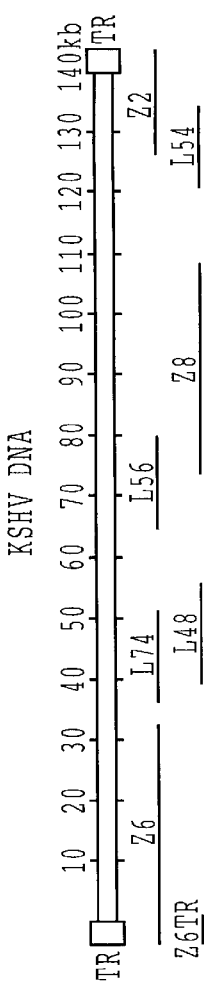
FIG. 2A
FIG. 2B

```
   1 atggcgcccc cgggaatgcg cctgaggtcg ggacggagca ccggcgcgcc cttaacgaga
  61 ggaagttgta ggaaacgaaa caggtctccg gaaagatgtg accttggcga tgacctacat
 121 ctacaaccgc gaaggaagca tgtcgccgac tccatcgacg gccgggaatg tggaccccac
 181 accttgccta tacctggaag tcccacagtg ttcatatccg ggctgccagc atttgtgtct
 241 agtcctactt taccggtggc tcccattcct tcacccgctc ccgcaacacc tttacctcca
 301 ccggcactct tacccccgt aaccacgtct tcctccccaa tccctccatc ccatcctgtg
 361 tctccgggga ccacggatac tcattctcca tctcctgcat tgccacccac gcagtctcca
 421 gagtcttctc aaaggccacc gctttcaagt cctacaggaa ggccagactc ttcaacacct
 481 atgcgtccgc cacccctcgca gcagactaca cctccacact caccacgac tcctccaccc
 541 gagcctccct ccaagtcgtc accagactct ttagctccgt ctaccctgcg tagcctgaga
 601 aaaagaaggc tatcgtcccc caaggtccc tctacactaa acccaatatg tcagtcgccc
 661 ccagtctctc cccctagatg tgacttcgcc aaccgtagtg tgtaccccc atgggccaca
 721 gagtccccga tctacgtggg atcatccagc gatggcgata ctccgccacg ccaaccgcct
 781 acatctccca tctccatagg atcatcatcc ccgtctgagg gatcctgggg tgatgacaca
 841 gccatgttgg tgctccttgc ggagattgca gaagaagcat ccaagaatga aaaagaatgt
 901 tccgaaaata atcaggctgg cgaggataat ggggacaacg agattagcaa ggaaagtcag
 961 gttgacaagg atgacaatga caataaggat gatgaggagg agcaggagac agatgaggag
1021 gacgaggagg atgacgagga ggatgacgag gaggatgacg aggaggatga cgaggaggat
1081 gacgaggagg atgacgagga ggatgacgag gaggatgacg aggaggatga cgaggaggat
1141 gacgaggagg atgacgagga ggaggacgag gaggaggacg aggaggagga cgaggaggag
1201 gaggacgagg aggatgacga tgatgaggac aatgaggacg aggaggatga cgaggaggag
1261 gacaagaagg aggacgagga ggacgggggc gatggaaaca aacgttgag catccaaagt
1321 tcacaacagc agcaggagcc acaacagcag gagccacagc agcaggagcc acagcagcag
1381 gagcccctgc aggagccaca acagcaggag ccacagcagc aggagccaca gcagcaggag
1441 cccctgcagg agccacaaca gcaggagcca cagcagcagg agcccctgca ggagccacaa
1501 cagcaggagc cacaacagca ggagccacag cagcaggagc cacagcagca ggagccacag
1561 cagcaggagc cacagcagca ggagccacag cagcaggagc cacagcagca ggagccacag
1621 cagcaggagc cacagcagca ggagccacag cagcgggagc cacagcagcg ggagccccag
1681 cagcgggagc cacagcagcg ggagccacag cagcgggagc cacagcagcg ggagccacag
1741 cagcgggagc cacagcagcg ggagccacag cagcgggagc cacagcagca ggatgagcag
1801 cagcaggatg agcagcagca ggatgagcag cagcaggatg agcagcagca ggatgagcag
1861 cagcaggatg agcagcagca ggatgagcag cagcaggatg agcagcagca ggatgagcag
1921 cagcaggatg agcagcagca ggatgagcag cagcaggatg agcagcagca ggatgagcag
1981 cagcaggatg agcagcagca ggatgagcag cagcaggatg agcagcagca ggatgagcag
2041 cagcaggatg agcagcagca ggatgagcag cagcaggatg agcagcagca ggatgagcag
2101 gagcagcagg atgagcagga gcagcaggat gagcaggagc agcaggatga gcagcagcag
2161 gatgagcagc agcagcagga tgagcagcag cagcaggatg agcagcagca gcaggatgag
2221 cagcagcagc aggatgagca gcagcagcag gatgaacagg agcagcagga ggagcaggag
2281 cagcaggagg agcaggagca ggagttagag gagcaggagc aggagttaga ggatcaggag
2341 caggagttag aggagcagga gcaggagtta ggagcaggag gcaggagtt agaggagcag
2401 gagcaggagt tagaggagca ggagcaggag ttagaggagc aggagcagga gttagaggag
2461 caggagcagg agttagagga gcaggagcag gagttagagg agcaggagca ggagttagag
2521 gagcaggagg tggaagagca agagcaggag gtggaagagc aagagcagga gcaggaagag
```

FIG. 9A

```
2581 caggaattag aggaggtgga ggagcaagag caggagcagg aggagcagga ggagcaggag
2641 ttagaggagg tggaagagca ggaagagcag gagttagagg aggtggaaga gcaggaagag
2701 caggagttag aggaggtgga agagcaggag cagcaggagt tagaggaggt ggaagagcag
2761 gagcagcagg gggtggaaca gcaggagcag gagacggtgg aagagcccat aatcttgcac
2821 gggtcgtcat ccgaggacga aatggaagtg gattaccctg ttgttagcac acatgaacaa
2881 attgccagta gcccaccagg agataataca ccagacgatg acccacaacc tggcccatct
2941 cgcgaatacc gctatgtact cagaacatca ccaccccaca gacctggagt tcgtatgagg
3001 cgcgttccag ttacccaccc aaaaaagcca catccaagat accaacaacc accggtccct
3061 tacagacaga tagatgattg tcctgcgaaa gctaggccac aacacatctt ttatagacgc
3121 tttttgggaa aggatggaag acgagatcca aagtgtcaat ggaagtttgc agtgattttt
3181 tggggcaatg acccatacgg acttaaaaaa ttatctcagg ccttccagtt tggaggagta
3241 aaggcaggcc ccgtgtcctg cttgccccac cctggaccag accagtcgcc cataacttat
3301 tgtgtatatg tgtattgtca gaacaaagac acaagtaaga aagtacaaat ggcccgccta
3361 gcctgggaag ctagtcaccc cctggcagga aacctacaat cttccatagt taagtttaaa
3421 aagcccctgc cattaaccca gccaggggaa aaccaaggtc ctggggactc tccacaggaa
3481 atgacataa
```

FIG. 9A
(CONT.)

MAPPGMRLRSGRSTGAPLTRGSCRKRNRSPERCDLGDDLHLQPR
RKHVADSIDGRECGPHTLPIPGSPTVFTSGLPAFVSSPTLPVAPIPSPAPATPLPPPA
LLPPVTTSSSPIPPSHPVSPGTTDTHSPSPALPPTQSPESSQRPPLSSPTGRPDSSTP
MRPPPSQQTTPPHSPTTPPPEPPSKSSPDSLAPSTLRSLRKRRLSSPQGPSTLNPICQ
SPPVSPPRCDFANRSVYPPWATESPIYVGSSSDGDTPPRQPPTSPISIGSSSPSEGSW
GDDTAMLVLLAEIAEEASKNEKECSENNQAGEDNGDNEISKESQVDKDDNDNKDDEEE
QETDEEDEEDDEEDDEEDDEEDDEEDDEEDDEEDDEEDDEEDDEEDDEEDDEEEDEEE
DEEEDEEEEDEEDDDDEDNEDEEDDEEEDKKEDEEDGGDGNKTLSIQSSQQQQEPQQQ
EPQQQEPQQQEPLQEPQQQEPQQQEPQQQEPLQEPQQQEPQQQEPLQEPQQQEPQQQE
PQQQEPQQQEPQQQEPQQQEPQQQEPQQQEPQQQEPQQQEPQQREPQQREPQQREPQQ
REPQQREPQQREPQQREPQQREPQQREPQQQDEQQQDEQQQDEQQQDEQQQDEQQQDE
QQQDEQQQDEQQQDEQQQDEQQQDEQQQDEQQQDEQQQDEQQQDEQQQDEQQQDEQQQ
DEQQQDEQQQDEQQQDEQEQQDEQEQQDEQEQQDEQQQDEQQQQDEQQQQDEQQQQDE
QQQQDEQQQQDEQEQQEEQEQQEEQEQELEEQEQELEDQEQELEEQEQELEEQEQELE
EQEQELEEQEQELEEQEQELEEQEQELEEQEQELEEQEVEEQEQEVEEQEQ
EQEEQELEEVEEQEQEEQEEQELEEVEEQEEQELEEVEEQEEQELEEVEEQEQQEL
EEVEEQEQQGVEQQEQETVEEPIILHGSSSEDEMEVDYPVVSTHEQIASSPPGDNTPD
DDPQPGPSREYRYVLRTSPPHRPGVRMRRVPVTHPKKPHPRYQQPPVPYRQIDDCPAK
ARPQHIFYRRFLGKDGRRDPKCQWKFAVIFWGNDPYGLKKLSQAFQFGGVKAGPVSCL
PHPGPDQSPITYCVYVYCQNKDTSKKVQMARLAWEASHPLAGNLQSSIVKFKKPLPLT
QPGENQGPGDSPQEMT

FIG. 9B

EBNA1

```
        atgtctgacga ggggccaggt acaggacctg gaaatggcct aggagagaag
108001  ggagacacat ctggaccaga aggctccggc ggcagtggac ctcaaagaag aggggtgat
108061  aaccatggac gaggacgggg aagaggacga ggacgaggag gcggaagacc aggagccccg
108121  ggcggctcag gatcagggcc aagacataga gatggtgtcc ggagacccca aaaacgtcca
108181  agttgcattg gctgcaaagg gacccacggt ggaacaggag caggagcagg agcgggaggg
108241  gcaggagcag gagggggcagg agcaggagga ggggcaggag caggaggagg ggcaggaggg
108301  gcaggagggg caggaggggc aggagcagga ggaggggcag gagcaggagg aggggcagga
108361  ggggcaggag gggcaggagc aggaggaggg gcaggagcag gaggaggggc aggaggggca
108421  ggagcaggag gaggggcagg aggggcagga ggggcaggag caggaggagg ggcaggagca
108481  ggaggagggg caggaggggc aggagcagga ggaggggcag gaggggcagg aggggcagga
108541  gcaggaggag gggcaggagc aggaggggca ggaggggcag gaggggcagg agcaggaggg
108601  gcaggagcag gaggaggggc aggaggggca ggaggggcag gagcaggagg ggcaggagca
108661  ggaggggcag gagcaggagg ggcaggagca ggaggggcag gaggggcagg agcaggaggg
108721  gcaggagggg caggagcagg agggcagga gggcaggag caggaggagg ggcaggaggg
108781  gcaggagcag gaggaggggc aggaggggca ggagcaggag gggcaggagg ggcaggagca
108841  ggaggggcag gaggggcagg agcaggaggg gcaggagggg caggagcagg aggaggggca
108901  ggagcaggag gggcaggagc aggaggtgga ggccggggtc gaggaggcag tggaggccgg
108961  ggtcgaggag gtagtggagg ccggggtcga ggaggtagtg gaggccgccg gggtagagga
109021  cgtgaaagag ccagggggg aagtcgtgaa agagccaggg ggagaggtcg tggacgtgga
109081  gaaaagaggc ccaggagtcc cagtagtcag tcatcatcat ccgggtctcc accgcgcagg
109141  ccccctccag gtagaaggcc attttttccac cctgtagggg aagccgatta ttttgaatac
109201  caccaagaag gtggcccaga tggtgagcct gacgtgcccc cgggagcgat agagcagggc
109261  cccgcagatg acccaggaga aggcccaagc actggacccc ggggtcaggg tgatggaggc
109321  aggcgcaaaa aaggagggtg gtttggaaag catcgtggtc aaggaggttc caacccgaaa
109381  tttgagaaca ttgcagaagg tttaagagct ctcctggcta ggagtcacgt agaaaggact
109441  accgacgaag gaacttgggt cgccggtgtg ttcgtatatg gaggtagtaa gacctccctt
109501  tacaacctaa ggcgaggaac tgcccttgct attccacaat gtcgtcttac accattgagt
109561  cgtctccct ttggaatggc ccctggaccc ggcccacaac ctggcccgct aagggagtcc
109621  attgtctgtt atttcatggt cttttacaa actcatatat ttgctgaggt tttgaaggat
109681  gcgattaagg accttgttat gacaaagccc gctcctacct gcaatatcag ggtgactgtg
109741  tgcagctttg acgatggagt agatttgcct ccctggttc cacctatggt ggaagggct
109801  gccgcggagg gtgatgacgg agatgacgga gatgaaggag gtgatggaga tgagggtgag
109861  gaagggcagg agtga
```

FIG. 9C

```
         10        20        30        40        50        60        70
         |         |         |         |         |         |         |
MSDEGPGTGPGNGLGEKGTSGPEGSGSGPEGSSGSGPQRRGGDNHGRGRGRGRGGGRPGAPGGSGSGPRHRDGV  70
RRPQKRPSCIGCKGTHGGTGEGAGAGAGGAGGAGAGGAGGAGGAGAGGAGGAGAGGAGGAGAGGAGGAGGAG  140
GAGAGGAGAGGAGGAGAGGAGGAGAGGAGGAGAGGAGGAGAGGAGGAGAGGAGGAGAGGAGGAGAGGAGGA  210
GGAGAGGAGGAGAGGAGGAGAGGAGGAGAGGAGGAGAGGAGGAGAGGAGGAGAGGGGRGRGGSGGGRGRGGS  280
GGGAGGAGAGGAGGAGAGGGGAGAGGGAGGGGRGRGGSGGGRGGSSGGGRGGSGGGRGRGGSGGGRGRGGS  350

360       370       380       390       400       410       420
         |         |         |         |         |         |         |
GGRRGRGRERARGGSRERARGRGRGEKRPRSPSSQSSSSGSPPRRPPPGRRPFHPVGEADYFEYHQE  420
GGPDGEPDVPPGAIECGPADDPGEGPSTGPRGDGGRRKKGGWFGKHRGCGGSNPKFENIAEGLRALLA  490
RSHVERTTDEGTWVAGVFVYGGSKTSLYNLRRGTALAIPQCRLTPLSRLPFGMAPGPGPQPGPLRESIVC  560
YFMVFLQTHIFAEVLKDAIKDLVMTKPAPTCNIRVTVCSFDDGVDLPPWFPPMVEGAAAEGDDGDDGDEG  630
GDGDEGEEGQE  641
```

FIG. 9D

METHODS TO INHIBIT OR ENHANCE THE BINDING OF VIRAL DNA TO GENOMIC HOST DNA

This invention was made in part with government support from a public service grant NCI CA72150-01. The government has certain rights in the invention.

FIELD OF THE INVENTION

This invention generally relates to novel compounds and methods for the detection of compounds that are agonistic or antagonistic for the binding of viral genetic material to genomic host DNA. Additionally, the inventions generally relates to compounds and methods related to gene transfer and gene therapy, as well as therapeutics for virally based diseases.

BACKGROUND

In 1872, Moritz Kaposi described a multifocal vascular tumor affecting elderly men of Mediterranean or Eastern European origin. More recently, this neoplasm has become prevalent in immunocompromised patients, such as transplant recipients on immunosuppressive therapy, and AIDS patients, where it has become the most common cancer (Beral, V. "Epidemiology of Kaposi's sarcoma" *Cancer Surv* 10:5–22, 1991). The relationship of the disease to geography and immunocompromised patients led to the suspicion of an infectious agent in Kaposi's sarcoma pathogenesis. This suspicion was supported when KSHV or human herpesvirus 8 (HHV8) was identified through PCR based studies of tumor samples from AIDS patients with Kaposi's sarcoma (Chang, Y. et al. "Identification of herpesvirus-like DNA sequences in AIDS-associated Kaposi's sarcoma" *Science* 266:1865–1869, 1994). Subsequent studies have shown that the virus is of the gammaherpesviridae family, bearing sequence similarity to herpesvirus saimiri (HVS) and Epstein-Barr virus (EBV) (Russo, J. "Nucleotide sequence of the Kaposi sarcoma-associated herpesvirus (HHV8)" *PNAS* 93:14862–14867, 1996). Although there is increasing epidemiologic data associating the virus with human disease, little is known about the biology of this new gammaherpesvirus.

Indirect immunofluorescence studies of the latently infected BCBL cell line with serum from KS patients reveals a characteristic punctate pattern of nuclear immunofluorescence due to the presence of what was termed the latency-associated nuclear antigen (LANA) (Moore, P. S., et al. "Primary characterization of a herpesvirus agent with Kaposi's sarcoma" *J Virol* 70:549–558, 1996; Simpson, G. R. et al. "Prevalence of Kaposi's sarcoma associated herpesvirus infection measured by antibodies to recombinant capsid protein and latent immunofluorescence antigen" *Lancet* 348:1133–1138, 1996). LANA is detected in the majority of cells in a KS lesion as well as in cell lines derived from body cavity lymphomas (Simpson, G. R. et al. "Prevalence of Kaposi's sarcoma associated herpesvirus infection measured by antibodies to recombinant capsid protein and latent immunofluorescence antigen" *Lancet* 348:1133–1138, 1996; Rainbow, L., et al. "The 222- to 234-kilodalton latent nuclear protein (LNA) of Kaposi's sarcoma-associated herpesvirus (human herpes 8) is encoded by orf73 and is a component of the latency-associated nuclear antigen" *J Virol* 71:5915–5921, 1997). Studies based on the detection of antibodies to LANA have shown that KSHV infection precedes onset of KS and other associated lymphoproliferative diseases (Gao, S. J., et al. "Seroconversion to antibodies against Kaposi's sarcoma-associated herpesvirus-related latent nuclear antigens before the development of Kaposi's sarcoma" *N Engl J Med* 335:223–241, 1996). LANA is encoded by orf73 of KSHV and is expressed as a latency-associated protein in the infected cell (Rainbow, L., et al. "The 222- to 234-kilodalton latent nuclear protein (LNA) of Kaposi's sarcoma-associated herpesvirus (human herpes 8) is encoded by orf73 and is a component of the latency-associated nuclear antigen" *J Virol* 71:5915–5921, 1997; Kedes, D. H., et al. "Identification of the gene encoding the major latency-associated nuclear antigen of the Kaposi's sarcoma-associated herpesvirus" *J Clin Invest* 100:2606–2610, 1997). An analysis of the LANA amino acid sequence reveals several acidic and proline/glutamine rich regions as well as a zinc finger DNA binding domain (Neipel, F., et al. "Fleckenstein Cell-homologous genes in the Kaposi's sarcoma-associated rhadinovirus human herpesvirus 8: determinants of its pathogenicity?" *J Virol* 71:4187–4192, 1997; Ganem, D. "KSHV and Kaposi's sarcoma: the end of the beginning of the end?" *Cell* 91:157–160, 1997). In spite of this suggestion that LANA may act as a transcription factor, a specific function is yet to be assigned for this viral protein.

Little is known regarding the mechanism and establishment of KSHV latency. However, the persistence of the viral genome through generations of host cell divisions potentiates the host's propensity of contracting the disease encoded by the virus. What is needed is a drug screen for agents that would disrupt the ability of a viral genome (e.g. the KSHV genome) to bind to host DNA thereby eliminating the viral genome in the host.

SUMMARY OF THE INVENTION

The present invention generally comprises novel compounds and methods to screen for compounds that interfere with the ability of viral genomic DNA or RNA to bind to host genomic DNA. Additionally, the present invention relates to the targeting of genes to host genomes in gene therapy applications. Furthermore, the present invention relates to compositions and methods for the treatment of viral infections and tumors.

Genomic DNA from latent viruses is able to persist for multiple generations of the host cell by binding to a tethering protein that is encoded by the viral DNA. We have discovered the mechanism of binding of the viral DNA to the host cell. For example, genomic DNA from the Kaposi sarcoma virus (KSHV) is able to persist for multiple generations of the host cell by binding to a tethering protein, the latency-associated nuclear antigen (LANA). LANA tethers the KSHV viral DNA to the chromosomal structural protein, histone 1 (H1). LANA is encoded by the viral DNA, therefore it will only be present in a host cell after infection. Likewise, the lack of LANA in a host cell would indicate the lack of viral infection by viruses that utilize this or similar proteins to ensure persistence. LANA binds to specific locations on the KSHV genomic DNA designated Z6, Z8 and Z2. We have defined three other smaller binding regions that partially overlap with Z6, Z8 and Z2, which we have named LBR1 (LANA binding region 1), LBR2, LBR3 and LBR4. These regions are located at approximately 22–27 kb, 109–111 kb, 127–132 kb and a region at the left 1.8 kb of the KSHV genome including one copy of the terminal repeat, respectively. LBR1 is located within the Z1 binding region, LBR2 is located immediately 3' to the Z8 binding region and LBR3 is located within the Z2 binding region. The Epstein Bar Virus (EBV) persists in host cells by a similar mechanism in that it utilizes a tethering protein (EBNA1) to bind the viral genomic DNA to host histone H1 proteins. These discoveries will permit (among other things) the screening of agents that interfere with viral DNA binding to host DNA.

As noted above, the present invention also contemplates screening assays to identify drugs that inhibit or potentiate the binding of tethering proteins (e.g. LANA and EBNA1) to host histone H1 proteins. A variety of assay formats are contemplated for testing the potential of compounds suspected of modulating tethering protein binding. In one embodiment, cells are pretreated with the compound suspected of modulating the binding of the tethering protein, followed by the addition of viral DNA or viruses that encode the tethering protein. A cell free assay for the screening of drugs that inhibit or potentiate the binding of tethering proteins (e.g. LANA and EBNA1) to host histone H1 proteins is contemplated by the present invention. For example, providing i) histone H1 proteins and ii) LANA or EBNA1; adding a compound or compounds suspected of inhibiting or potentiating the binding of LANA or EBNA1 to histone H1; and detecting said binding (e.g., by Western blot).

The invention is not limited to any particular measurement technique to measured bound tethering protein. Various methods are envisioned. In one embodiment, immunofluorescence is used. In another embodiment, immunoprecipitation is used. Compounds that inhibit tethering protein binding will reveal less bound tethering protein as compared to controls. Compounds that potentiate the binding of tethering protein will reveal increased bound tethering protein as compared to controls. The present invention also contemplates the use of high throughput screening methods. For example, the use of robotics or computer controlled systems are contemplated.

The present invention is not limited to any particular mechanism by which the viral DNA binds to the host cell. For example, the compound may inhibit the binding of the viral DNA by competitively inhibiting said binding at the binding site, by sequestering the viral DNA, or by sequestering the tethering protein.

It is not intended that the present invention be limited by the nature of the compounds to be screened in the screening assay of the present invention. For example, a variety of compounds including oligonucleotides, peptides, organic compounds and nonorganic compounds, are contemplated. Additionally, combinations of compounds are contemplated by the present invention.

It is not intended that the screening assays of the present invention be limited to any particular virus or viral genome. Many different viruses are contemplated to be used in the screening assays.

It is not intended that the screening assays of the present invention be limited to any particular host cell. Many different host cells are contemplated by the present invention to be used in the screening assays.

It is not intended that the screening assays of the present invention be limited to any particular tethering protein. Many different types of tethering proteins are contemplated to be use and detected by the present invention.

The invention contemplates compounds and methods to be used in gene directed therapy. For example, the invention contemplates the use of the LANA tethering protein (or portion thereof) in conjunction with the KSHV LANA DNA binding sites for the purpose of targeting DNA that encodes therapeutic proteins to the chromosomes of the host cell. The ability of LANA to bind histone H1, when used in combination with the a gene therapy vector containing a therapeutic protein and the specific KSHV genomic binding regions, will ensure the inclusion and persistence of the gene sequence in the host cell. It is not intended that the present invention be limited to LANA as the tethering protein. The use of other tethering proteins, such as EBNA1, is contemplated.

The invention also contemplates compounds and methods to be used in gene directed therapy where the LANA or EBNA1 protein is coupled to the DNA to be incorporated into the host is bound to the DNA by chemical means. It is not intended that the present invention be limited to a particular chemical means to bind the LANA protein to the DNA. For example, proteins may be ligated to nucleic acids via disulfide bonds (Chu, B. C. and Orgel, L. E. "Ligation of oligonucleotides to nucleic acids or proteins via disulfide bonds" *Nucl Acid Res* 16:3671–3691, 1988). It is not intended that the present invention be limited to any particular sequence of DNA to which the tethering protein may be chemically linked. For example, DNA sequences without the KSHV and EBV binding sites may be used.

It is not intended that the present invention be limited to a particular gene therapy. Many different types of gene therapies are contemplated by the present invention. It is not intended that the invention be limited to any particular disease. Many diseases are envisioned as potentially treatable with the present invention. For example, multiple sclerosis, Parkinson's disease, Huntington's disease, diabetes and other degenerative diseases are envisioned as being candidates for treatment with the present invention.

It is not intended that the gene therapy of the present invention be limited to any particular tethering protein. Many different types of tethering proteins, such as LANA and EBNA1, are contemplated to be used by the present invention.

It is not intended that the present invention be limited by the viral DNA binding sites used in the current invention providing the tethering protein recognizes the DNA binding sites.

The present invention contemplates compounds and methods for the treatment of viral infections. For example, it is contemplated that viral vectors can be produced that encode for tethering proteins (e.g. LANA and EBNA1) mutated to bind host histone H1 with greater avidity than wild type tethering proteins but bind viral DNA binding sites with reduced avidity or do not bind viral DNA binding sites. Such viral vectors would then block access to histone H1 sites thereby preventing infectious viral DNA from being replicated along with host DNA.

DESCRIPTION OF THE FIGURES

The file of this patent contains at least one drawing executed in color. Copies of this patent with color drawings will be provided by the Patent and Trademark Office upon request and payment of the necessary fee.

FIG. 2. LANA preferentially binds specific regions of the KSHV genome.

FIG. 9. Protein and nucleotide sequences of LANA and EBNA1. Panel (a) shows the nucleotide sequence of LANA (SEQ ID NO:1). Panel (b) shows the amino acid sequence of LANA (SEQ ID NO:2). Panel (c) shows the nucleotide sequence of EBNA1 (SEQ ID NO:3). Panel (d) shows the amino acid sequence of EBNA1 (SEQ ID NO:4).

DEFINITIONS

Figure 1:
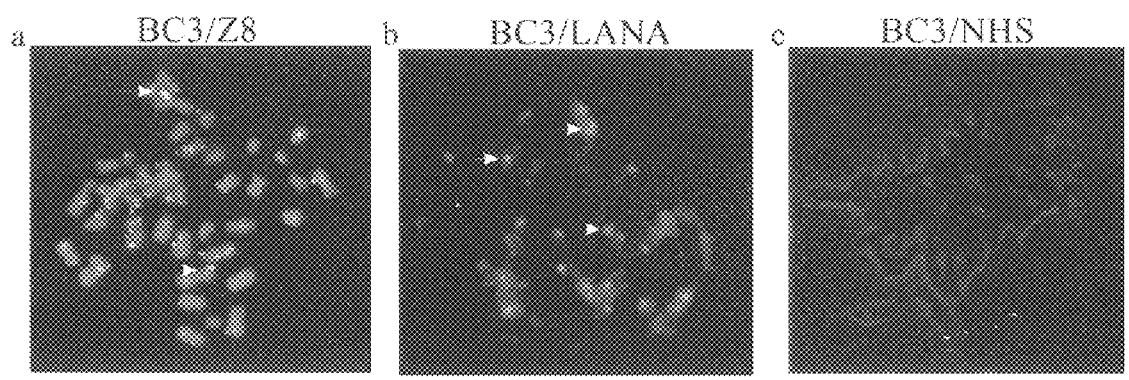
FIG. 1. KSHV DNA is associated with chromosomes in a similar pattern to LANA.

To facilitate understanding of the invention, a number of terms are defined below.

As used herein "virus", "viral" or "virus particle" is used to denote a group of infectious agents characterized by their inability to reproduce outside of a living host cell. Viruses may subvert the host cell's normal functions, causing the cell to behave in a manner determined by the virus. Likewise, the viral DNA may be "latent", being reproduced along with the host DNA without causing undue harm on the host cell. Additionally, viruses may be constructed in a laboratory using recombinant DNA or RNA and preexisting viral coats.

As used herein "host cell" is used to denote a cell that has been infected by one or more virus particles. The virus particles may be wild type or mutated.

As used herein "tethering protein" is used to denote a protein that functions to attach one or more molecules (e.g host DNA or host chromosomal proteins) to one or more other molecules (e.g. expression vectors for viral DNA). The tethering protein may have other functions in the cell in addition to functioning as a tethering protein.

As used herein "expression vector", "recombinant DNA vector" or "vector" is used herein to refer to DNA sequences containing a desired coding sequence and appropriate DNA sequences necessary for the expression of the operably linked coding sequence in a particular host organism (e.g., mammal). DNA sequences necessary for expression in procaryotes include a promoter, optionally an operator sequence, a ribosome binding site and possibly other sequences. Eukaryotic cells are known to utilize promoters, polyadenlyation signals and enhancers.

The phrase "gain-of-function" (gof) as used herein is applicable to the situation where a modified oligonucleotide that, when transfected into a host organism and translated into a peptide, results in a peptide that will function with increased efficiency (e.g. rate of reaction, affinity, etc.) as compared to the wild type peptide. For example, the modified oligonucleotide (or "gof nucleotide") may, in effect, function as an augmenter of the natural gene if the natural gene is present and functional in the host into which the gof oligonucleotide was transfected, or it may add that function to the host if the natural gene is not present or is non-functional.

The phrase "loss-of-function" (lof) as used herein is applicable to the situation where a modified oligonucleotide, when transfected into a host organism and translated into a peptide, results in a peptide that function with decreased efficiency (e.g. rate of reaction, affinity, etc.) as compared to the wild type peptide. For example, the modified oligonucleotide (or "lof" oligonucleotide") may, in effect, function as a diminisher of natural gene function if the natural gene is present and functional in the host into which the lof oligonucleotide was transfected, or may negatively interfere with processes in the host if the natural gene is not present or is non-functional.

As used herein "agent" or "drug" is used to denote a chemical compound (substance), a mixture of chemical compounds, a biological macromolecule, or an extract made from biological materials such as bacteria, plants, fungi, or animal (particularly mammalian) cells or tissues that are suspected of having therapeutic properties. The agent or drug may be purified, substantially purified or partially purified.

As used herein "agonist" refers to molecules or compounds which mimic the action of a "native" or "natural" compound. Agonists may be homologous to these natural compounds in respect to conformation, charge or other characteristics.

As used herein "antagonist" refers to molecules or compounds which inhibit the action of a "native" or "natural" compound. Antagonists may or may not be homologous to these natural compounds in respect to conformation, charge or other characteristics. As used herein, the term "fusion protein" refers to a chimeric protein containing the protein of interest joined to an exogenous protein fragment. The fusion partner may provide a detectable moiety, may provide an affinity tag to allow purification of the recombinant fusion protein from the host cell, or both. If desired, the fusion protein may be removed from the protein of interest by a variety of enzymatic or chemical means known to the art. The present invention contemplates portions of LANA and EBNA1 for fusion proteins.

As used herein, the term "purified" or "to purify" refers to the removal of contaminants from a sample. The present invention contemplates purified compositions (discussed above).

As used herein, the term "partially purified" refers to the removal of a moderate portion of the contaminants of a sample to the extent that the substance of interest is recognizable by techniques known to those skilled in the art as accounting for an amount of the mixture greater than approximately 5% of the total.

As used herein, the term "substantially purified" refers to the removal of a significant portion of the contaminants of a sample to the extent that the substance of interest is recognizable by techniques known to those skilled in the art as the most abundant substance in the mixture.

As used herein the term "portion" when in reference to a protein (as in "a portion of a given protein") refers to fragments of that protein. The fragments may range in size from four amino acid residues to the entire amino acid sequence minus one amino acid. In one embodiment, the present invention contemplates "functional portions" of a protein. Such portions are "functional" if they contain a binding region (i.e. a region having affinity for another molecule) and such binding can take place (i.e. the binding region functions, albeit with perhaps lower affinity than that observed for the full-length protein). Such "functional portions" of the gene product are typically greater than approximately 10 amino acids in length, and more typically greater than approximately 50 amino acids in length, and even more typically greater than approximately 100 amino acids in length. "Functional portions" may also be "conserved portions" of the protein. The alignment of the various gene products permit one skilled in the art to select conserved portions of the protein (i.e. those portions in common between two or more species) as well as unconserved portions (i.e. those portions unique to two or more species). The present invention contemplates conserved portions 10 amino acids in length or greater, and more typically greater than 50 amino acids in length.

"Staining" shall be defined as any number of processes known to those in the field that are used to better visualize, distinguish or identify a specific component(s) and/or feature(s) of a cell or cells.

"Immunofluorescence" is a staining technique used to identify, mark, label, visualize or make readily apparent by procedures known to those practiced in the art, where a ligand (usually an antibody) is bound to a receptor (usually an antigen) and such ligand, if an antibody, is conjugated to a fluorescent molecule, or the ligand is then bound by an antibody specific for the ligand, and said antibody is conjugated to a fluorescent molecule, where said fluorescent molecule can be visualized with the appropriate instrument (e.g. a fluorescent microscope).

"Immunoprecipitation" is a technique used to identify, mark, label, visualize or purify (or partially purify) by procedures known to those practiced in the art, where a ligand (usually an antibody) is bound to a receptor (usually an antigen) and such ligand, if an antibody, is conjugated to a carrier (e.g. protein A-sepharose), or the ligand is then bound by an antibody specific for the ligand, and said antibody is conjugated to a carrier, where the precipitated molecule can the be released from the antibody, if desired.

"Antibody" shall be defined as a glycoprotein produced by B cells that binds with high specificity to the agent (usually, but not always, a peptide), or a structurally similar agent, that generated its production. Antibodies may be produced by any of the known methodologies [Current Protocols in Immunology (1998) John Wiley and Sons, Inc., N.Y.] and may be either polyclonal or monoclonal.

"In operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

"Antigen" shall be defined as a protein, glycoprotein, lipoprotein, lipid or other substance that is reactive with an antibody specific for a portion of the molecule.

"Morphology" shall be defined as the visual appearance of a cell or organism when viewed with the eye, a light microscope, a confocal microscope or an electron-microscope, as appropriate.

"Patient" shall be defined as a human or other animal, such as a guinea pig or mouse and the like.

A "wild type" cell or cell line shall be defined as a cell or cell line that retains the characteristics normally associated with that type of cell or cell line for the physiological process or morphological characteristic that is being examined. It is permissible for the cell or cell line to have non-wild type characteristics for physiological process or morphological characteristics that are not being examined as long as they do not appreciably affect the process or characteristic being examined.

"Tether" and "tethering" shall be defined as the ability of a compound (e.g. a protein) to attach (bind) to a first binding partner (e.g. an oligonucleotide) and to a second binding partner (e.g. a second oligonucleotide or a second protein). Such tethering may be reversible or nonreversible.

"Host" shall be defined as a receipient cell or organism.

A compound "suspected of modulating the interaction" of two or more molecules shall be defined as a chemical compound or substance the may increase or decrease binding affinity or avidity of said two or more molecules, inhibit binding either competitively, noncompetitively or allostericly of said two or more molecules, or alter the temperature, pH, salt concentration or ion concentration at which said two or more molecules interact.

GENERAL DESCRIPTION OF THE INVENTION

Figure 6:
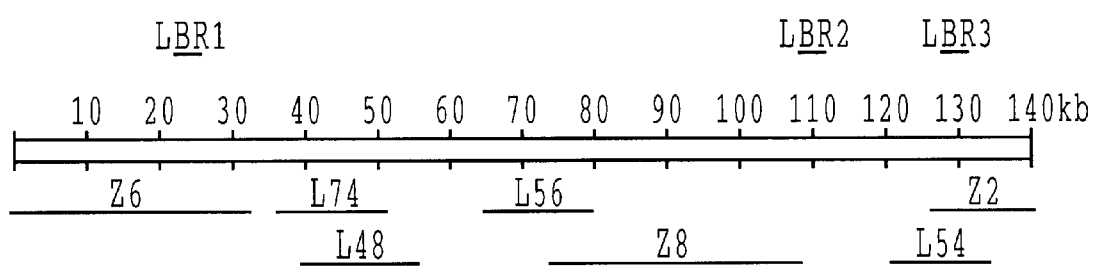
FIG. 6. Location of three specific LANA binding regions (LBR) within the KSHV genome.

The data present in this application demonstrate that the KSHV genome is tethered to the host chromosome through its interaction with LANA. Furthermore, it was demonstrated that LANA binds preferentially to cis-acting elements located within the Z2 KSHV cosmid probe and that chromatin localization depends on the presence of both LANA and Z2. Finally, the immunoprecipitation data shows that LANA binds host histone H1 in body cavity lymphoma derived cells and in vitro. This interaction has two potentially important consequences. First, it provides the first biochemical link between KSHV episomes and host chromatin that may thereby confer persistence of the KSHV genome in daughter cells. Second, because histone H1 has increasingly been regarded as a modulator of eukaryotic transcription (Ramakrishnan, V., et al. "Histone structure and the organization of the nucleosome" *Annu Rev Biophys Biomol Struct* 26:83–112, 1997; Wolffe, A. P. "H1" *Intl J Biochem and Cellbio* 29:1463–1466, 1997), LANA may influence expression of H1 transcriptional targets through modulation of H1 transcriptional activities. These interactions lead us to assert a model describing a novel mechanism of viral latency, summarized in FIG. 6. Without limiting the invention to any particular mechanism, in this model, the KSHV encoded LANA tethers the KSHV episome (Renne, R., et al. "The size and conformation of Kaposi's sarcoma-associated herpesvirus (human herpesvirus 8) DNA in infected cells and virions" *J Virol* 70:8151–8154; Decker, L., et al. "The Kaposi sarcoma-associated herpesvirus (KSHV) is present as an intact latent genome in KS tissue but replicates in the peripheral blood mononuclear cells of KS patients" *J Exp Med* 184:283–288, 1996) to host chromosomes through interaction with the histone H1 and specific cis-acting elements located within the Z2 region of the genome.

A synthesis of data collected over several years reveals that such a mechanism of persistent infection is also possible in EBV infected cells. It is known that EBV episomes (Harris, A., et al. "Random associations of Epstein-Barr virus genomes with host cell metaphase chromosomes in Burkitt's lymphoma-derived cell lines" *J Virol* 56:328–332, 1985) and EBNA1 (Grogan, E. A., et al. "Two Epstein-Barr viral nuclear neoantigens distinguished by gene transfer, serology and chromosome binding" *PNAS* 80:7650–7653, 1983) are randomly associated with metaphase chromosomes. It has long been thought that EBNA1 was necessary for both viral persistence and replication. However, recent studies suggest that EBNA 1 does not recruit replicative machinery to oriP and may not be required for replication (Aiyar, A., et al. "The plasmid replicon of EBV consists of multiple cis-acting elements that facilitate DNA synthesis by the cell and a viral maintenance element" *EMBO* 17:63940–6403, 1998). EBNA 1, however, allows persistence of oriP containing plasmids. Additionally, histone H1 was identified in a one-hybrid screen for proteins that interact with EBNA 1 bound to oriP (Aiyar, A., et al. "The plasmid replicon of EBV consists of multiple cis-acting elements that facilitate DNA synthesis by the cell and a viral maintenance element" *EMBO* 17:63940–6403, 1998). In spite of all these data, colocalization of EBNA1 and EBV to chromosomes as well as the biochemical basis of their association with chromosomes have not been demonstrated.

Sugden and colleagues hypothesized that EBNA 1 binds to specific DNA sequences on EBV and links this bound DNA through its many linking domains by interacting with chromosome associated proteins (Aiyar, A., et al. "The plasmid replicon of EBV consists of multiple cis-acting elements that facilitate DNA synthesis by the cell and a viral maintenance element" *EMBO* 17:63940–6403, 1998). LANA may exhibit analogous functions to EBNA1 in linking KSHV episomes to host chromosomes thereby ensuring control of copy number, segregation, and persistence in the infected cell. LANA may also function as a viral defense against cellular pathways evolved to eliminate viral genetic material, similar to how EBNA 1 prevents over-whelming episomal loss in EBV infection (Aiyar, A., et al. "The plasmid replicon of EBV consists of multiple cis-acting elements that facilitate DNA synthesis by the cell and a viral maintenance element" *EMBO* 17:63940–6403, 1998).

DETAILED DESCRIPTION OF PREFERRED EMBODIMENTS

Generally, the nomenclature used hereafter and the laboratory procedures in cell culture, molecular genetics and nucleic acid chemistry and hybridization described below are those well known and commonly employed in the art. Standard techniques are used for recombinant nucleic acid methods, polynucleotide synthesis, microbial culture, viral culture and transformation (e.g. electroporation and lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N. Y., and Current Protocols in Molecular Biology (1996) John Wiley and Sons, Inc., N.Y.).

The present invention contemplates assays for detecting the ability of agents to inhibit or enhance the binding of viral DNA to host chromosomes where high-through-put screening formats are employed together with large agent banks (e.g. compound libraries, peptide libraries and the like) to identify antagonists or agonists. Such viral DNA binding antagonists and agonists may be further developed as potential therapeutics and diagnostic or prognostic tools for diverse types of acquired virally transmitted diseases. Additionally, the present invention contemplates compounds and methods useful for gene therapy and for the treatment of latent and non-latent viral infections.

1. Screens to Identify Agonists and Antagonists of Viral/Host DNA Binding Proteins There are several different approaches contemplated by the present invention to screen for small molecules that specifically inhibit or enhance the ability of latent viral oligonucleotides to bind to host cells. One approach is to culture the host cells in the presence of the compound using standard culture procedures, expose the treated host cells to the viral particles and then assay for the presence of a tethering protein (e.g. LANA or EBNA1) in the host chromosomes using assays known to those practiced in the art. Cultures of host cells that were untreated with the suspected compound or treated with carrier solution would serve as a negative control. The tethering protein could be detected in the host cells by, for example, immunofluorescence or western blotting. Viral DNA or RNA could be detected in the host cell, for example, by Southern blotting or northern blotting, respectively.

In another embodiment, a cell-free assay is contemplated. In one embodiment, this assay comprises, providing i) histone H1, ii) LANA or EBNA1 protein, and iii) a compound suspected of modulating the binding of said LANA or EBNA1 protein to histone H1; a) mixing, in operational condition, said histone H1 and said LANA or EBNA1 protein with said compound suspected of modulating the binding of LANA or EBNA1 to histone H1 and b) determining the binding of LANA or EBNA1 to histone H1 by, e.g., western blotting.

2. Methods Related to Gene Therapy

The present invention demonstrates that LANA and EBNA1 are sufficient to tether viral DNA to host cell histone H1 protein. Additionally, the present invention demonstrates that specific regions of the viral DNA are required for binding of LANA. This technology may be used in the delivery of therapeutic gene products thereby allowing for an effective method of gene therapy. In one embodiment, the host cells are obtained from an immunocompatible donor or from the patient. The host cells are transfected with a construct able to express the therapeutic protein of interest, (e.g. LANA, EBNA1 or other tethering protein) and the viral DNA binding sites for the tethering protein (e.g. Z6, Z2, Z8 or LANA specific consensus sites [LBR1, LBR2, LBR3; see experiment 6]). The use of the present invention would permit the transfected DNA that encodes for the therapeutic protein of interest to be replicated as the host cells divided, thereby circumventing the major problem with gene therapy, the elimination of the transfected DNA by the host cell. In another embodiment, portions of LANA or EBNA1 are chemically attached to DNA encoding the gene of interest. More specifically, for example, the protein may be ligated to a nucleotide encoding a gene of interest via disulfide bonds (Chu, B. C. and Orgel, L. E. "Ligation of oligonucleotides to nucleic acids or proteins via disulfide bonds" *Nucl Acids Res* 16:3671–3691, 1988). In yet another embodiment, nucleic acid operationally encoding the therapeutic gene of interest and a tethering protein such as LANA or EBNA1 may be administered to a host in absence of the viral protein coat. Details of these embodiments follow.

A. The Multicellular Organism

Any multicellular organism into which it may be desirable to introduce exogenous nucleic acid is a potential subject for the present invention. The multicellular organism may be a plant or an animal, preferably the latter. The animal is preferably a vertebrate animal, and more preferably a higher vertebrate, i.e., a mammal or bird, the former being especially preferred. Among mammals, preferred subjects are human and other primates, laboratory animals such as mice, rats, rabbits and hamsters, pet animals such as dogs and cats, and farm animals such as horses, cows, goats, pigs and sheep. It will be noted that these animals come from four orders of class Mammalia: Primata, Rodenta, Carnivora and Artiodactyla.

B. The Target Cell

The target cells may belong to tissues (including organs) of the organism, including cells belonging to (in the case of an animal) its nervous system (e.g., the brain, spinal cord and peripheral nervous cells), the circulatory system (e.g., the heart, vascular tissue and red and white blood cells), the digestive system (e.g., the stomach and intestines), the respiratory system (e.g., the nose and the lungs), the reproductive system, the endocrine system (the liver, spleen, thyroids, parathyroids), the skin, the muscles, or the connective tissue.

Alternatively, the cells may be cancer cells derived from any organ or tissue of the target organism, or cells of a parasite or pathogen infecting the organism, or virally infected cells of the organism.

A useful procedure for hepatic gene therapy requires an efficient and relatively non-invasive approach to the introduction of genes of interest into the liver. Several techniques, employing receptor mediated gene transfer, have been used with some success. However, there is a need for a readily reproducible procedure which results in the prolonged expression of the transgene in the liver, even in the absence of partial hepatectomy, and which therefore could be used for human gene therapy. Exogenous DNA has been introduced into hepatocytes of adult animals by targeting the asialoglycoprotein (ASGP) receptor by means of a ligand-poly-L-lysine biconjugate. For the ligand-targeting technique to be efficient, the DNA must be in a form which permits it to remain intact in the blood and is small enough to be recognized by the ASGP receptor on the surface of the hepatocytes. Wagner, et al. have targeted genes to the transferrin receptor in hepatoma cells by condensing the DNA with a poly-L-lysine/transferrin conjugate, into a complex with a diameter of 80–100 nm. This size DNA conjugate is appropriate for recognition by the transferrin receptor in hepatoma cells, but the ASGP receptor of hepatocytes discriminates against ligands larger than 10–20 nm in diameter.

A procedure for the introduction of genes into the liver of adult animals by receptor mediated uptake follows. This procedure has potential for application to human gene therapy. The major advantages of this method are: (i) the ease of preparation of the DNA complex; (ii) the ability to target genes to specific tissues; (iii) the prolonged expression of the gene in the liver; (iv) the relative safety of the complex, since it is devoid of infectious viral DNA; and (v) the episomal maintenance of the introduced gene.

C. Targeting i. Generally

In the absence of viral transfer of nucleic acid, compacted DNA may be targeted to a host cell or cells. "Targeting" is the administration of the compacted nucleic acid in such a manner that it enters the target cells in amounts effective to achieve the clinical purpose. In this regard, it should be noted that DNA and RNA are capable of replication in the nucleus of the target cell, and in consequence the ultimate level of the nucleic acid in the cell may increase after uptake. Moreover, if the clinical effect is mediated by a protein expressed by the nucleic acid, it should be noted that the nucleic acid acts as a template, and thus high levels of protein expression can be achieved even if the number of copies of the nucleic acid in the cell is low. Nonetheless, it is desirable to compact high concentrations of DNA to increase the number of target cells which take up the DNA and the number of DNA molecules taken up by each cell.

The route and site of administration may be chosen to enhance targeting. For example, to target muscle cells, intramuscular injection into the muscles of interest would be a logical choice. Lung cells might be targeted by administering the compacted DNA in aerosol form. The vascular endothelial cells could be targeted by coating a balloon catheter with the compacted DNA and mechanically introducing the DNA.

In some instances, the nucleic acid binding moiety, which maintains the nucleic acid in the compacted state, may also serve as a targeting agent. Polymers of positively charged amino acids are known to act as nuclear localization signals (NLS) in many nuclear proteins. Nonetheless, in some embodiments, targeting may be improved if a target cell binding moiety is employed.

ii. Use of Viral Transfer

The DNA may be packaged in a viral package (i.e. a viral protein coat encapsulating the DNA). Said viruses may be used to deliver the therapeutic DNA to the cells of interest. The therapeutic DNA may contain, in operation condition, a tissue specific promoter to ensure the expression of the therapeutic gene only in the tissue of interest. The present invention further contemplates the production of retroviral particles comprising modified (i.e., chimeric) envelope proteins containing protein sequences comprising a target binding moiety capable of binding to a receptor. Retrovirus particles bearing these modified envelope proteins may be used to deliver genes of interest to cells expressing the receptor. Retroviral particles bearing chimeric proteins containing peptide ligands and a portion of the envelope (env) protein of retroviruses (e.g., ecotropic Moloney murine leukemia virus or avian retroviruses) have been shown to be capable of binding to cells expressing the cognate receptor [Kasahara et al. (1994) *Science* 266:1373 and Valsesia-Wittmann et al. (1994) *J. Virol.* 68:4609].

iii. Use Of A Target Binding Moiety (TBM)

If a TBM is used, it must bind specifically to an accessible structure (the "receptor") of the intended target cells. While it is not necessary that it be absolutely specific for those cells, however, it must be sufficiently specific for the conjugate to be therapeutically effective. Preferably, its cross-reactivity with other cells is less than 20%, more preferably less than 10% and most preferably less than 5%.

There is no absolute minimum affinity which the TBM must have for an accessible structure of the target cell; however, the higher the affinity, the better. Preferably, the affinity is at least $10^3$ liters/mole, more preferably, at least $10^6$ liters/mole.

The TBM may be an antibody (or a specifically binding fragment of an antibody, such as an Fab, Fab, $V_M$, $V_L$ or CDR [complementarity-determination region]) which binds specifically to an epitope on the surface of the target cell. Methods for raising antibodies against cells, cell membranes, or isolated cell surface antigens are known in the art. Furthermore, the TBM may comprise a single-chain Fv which binds specifically to an epitope on the surface of the target cell. The single-chain Fv may comprise a fusion protein with a NABM (nucleic acid binding moiety) or a therapeutic protein sequence (e.g, an enzyme, cytokine, protein antibiotic, etc.).

The TBM may be a lectin, for which there is a cognate carbohydrate structure on the cell surface.

The target binding moiety may be a ligand which is specifically bound by a receptor carried by the target cells.

One class of ligands of interest are carbohydrates, especially mono- and oligosaccharides. Suitable ligands include galactose, lactose and mannose.

Another class of ligands of interest are peptides (which here includes proteins), such as insulin, epidermal growth factor(s), tumor necrosis factor, prolactin, chorionic gonadotropin, FSH, LH, glucagon, lactoferrin, transferrin, apolipoprotein E, gp120 and albumin.

The following table lists preferred target binding moieties for various classes of target cells:

| Target Cells | Target Binding Moiety |
|---|---|
| liver cells | galactose |
| Kupffer cells | mannose |
| macrophages | mannose |
| lung, liver, intestine | Fab fragment vs. polymeric immunoglobulin receptor (pIg R) |
| adipose tissue, | insulin |
| lymphocytes | Fab fragment vs. CD4 or gp120 |
| enterocyte | Vitamin B12 |
| muscle | insulin |
| fibroblasts | mannose-6-phosphate |
| nerve cells | Apolipoprotein E |

The target binding moiety may be encompassed with a larger peptide or protein. The use of a target binding moiety is not strictly necessary in the case of direct injection of the NABM/NA condensed complex. The target cell in this case is passively accessible to the NABM/NA condensed complex by the injection of the complex to the vicinity of the target cell.

iv. Liposome-Mediated Gene Transfer

The possibility of detecting gene expression by encapsulating DNA into a liposome (body contained by a lipid bilayer) using various lipid and solvent conditions, and injecting the liposome into animal tissues, has been demonstrated. However, despite the potential of this technique for a variety of biological systems, the DNA used in these experiments has not been modified or compacted to improve its survival in the cell, its uptake into the nucleus or its rate of transcription in the nucleus of the target cells. Thus, these procedures have usually resulted in only transient expression of the gene carried by the liposome.

Cationic lipids have been successfully used to transfer DNA. The cationic component of such lipids can compact DNA in solution. This method has been shown to result in heavily aggregated DNA complexes that, when used for transfecting the DNA in vitro, results in increased efficiency of gene transfer and expression (relative to naked DNA). Although the formation of these complexes can promote gene transfer in vitro, the injection of such complexes in vivo does not result in long lasting and efficient gene transfer.

A condensation procedure will provide structural features to the DNA/cationic lipid complex that will make it more amenable to prolonged in vivo expression. The combination of such methods could be accomplished by either of two procedures:

1. Formation of condensed DNA complex that is later encapsulated using neutral lipids into liposome bodies, or
2. Formation of highly condensed unimolecular DNA complexes upon condensation with cationic lipids could be accomplished. These complexes should provide a higher efficiency of gene transfer into tissues of animals in vivo.

The procedure of the present invention for the condensation of DNA, if coupled to the encapsulation of the resulting compacted DNA into a liposome body, could provide a variety of advantages for transfection into animals:

1. The liposome promotes the passive fusion with the lipid bilayer of the cytoplasmic membrane of mammalian cells in tissues.
2. The condensed DNA could then transfer the genetic information with a higher efficiency through the cell compartments to the nucleus for its expression.
3. Condensed DNA could be protected against degradation inside the cell, thus augmenting the duration of the expression of the newly introduced gene.
4. Possible immunological response to the polycation condensed DNA could be avoided by the encapsulation with the immunologically inert lipid bilayer.

D. The Nucleic Acid Binding Moiety

Any substance which binds reversibly or irreversibly to a nucleic acid may serve as the nucleic acid binding moiety (NABM), provided that (1) it binds sufficiently strongly and specifically to the nucleic acid to retain it until the conjugate reaches and enters the target cell, and does not, through its binding, substantially damage or alter the nucleic acid and (2) it reduces the interactions between the nucleic acid and the solvent, and thereby permits condensation to occur. The ultimate criterion is one of therapeutic effectiveness of the conjugate.

Preferably, the NABM is a tethering protein. More preferably, the NAMB is LANA or EBNA1. The NABM may also be a polycation. Its positively charged groups bind ionically to the negatively charged DNA, and the resulting charge neutralization reduces DNA-solvent interactions. A preferred polycation is polylysine. Other potential nucleic acid binding moieties include Arg-Lys mixed polymers, polyarginine, polyornithine, histones, avidin, and protamines.

E. The Nucleic Acid

Basic procedures for constructing recombinant DNA and RNA molecules in accordance with the present invention are disclosed by Sambrook, J. et al., In: *Molecular Cloning: A Laboratory Manual,* Second Edition, Cold Spring Harbor Press, Cold Spring Harbor, N.Y. (1989), which reference is herein incorporated by reference.

The nucleic acid may be a DNA, RNA, or a DNA or RNA derivative such as a derivative resistant to degradation in vivo, as discussed below. Within this specification, references to DNA apply to other nucleic acids as well, unless clearly forbidden by the context. The nucleic acid may be single or double stranded. It is preferably of 10 to 1,000,000 bases (or base pairs), more preferably 100 to 100,000, and the bases may be same or different. The bases may be the "normal" bases adenine (A), guanine (G), thymidine (T), cytosine (C) and uracil (U), or abnormal bases. The nucleic acid may be prepared by any desired procedure.

In a preferred embodiment, the nucleic acid comprises an expressible gene which is functional in the target cell, as well as a tethering protein (e.g. LANA or EBNA1). Examples of expressable genes may be, genes that encode coagulation factors, (such as Factor IX), enzymes involved in specific metabolic defects, (such as urea cycle enzymes, especially ornithine transcarbamylase, argininosuccinate synthase, and carbamyl phosphate synthase); receptors, (e.g., LDL receptor); toxins; thymidine kinase to ablate specific cells or tissues; ion channels (e.g., chloride channel of cystic fibrosis); membrane transporters (e.g., glucose transporter); and cytoskeletal proteins, (e.g., dystrophin). The gene may be of synthetic, cDNA or genomic origin, or a combination thereof. The gene may be one which occurs in nature, a non-naturally occurring gene which nonetheless encodes a naturally occurring polypeptide, or a gene which encodes a recognizable mutant of such a polypeptide. It may also encode an mRNA which will be "antisense" to a DNA found or an mRNA normally transcribed in the host cell, but which antisense RNA is not itself translatable into a functional protein.

For the gene to be expressible, the coding sequence must be operably linked to a promoter sequence functional in the target cell. Two DNA sequences (such as a promoter region sequence and a coding sequence) are said to be operably linked if the nature of the linkage between the two DNA sequences does not (1) result in the introduction of a frame-shift mutation in the region sequence to direct the transcription of the desired gene sequence, or (3) interfere with the ability of the gene sequence to be transcribed by the promoter region sequence. A promoter region would be operably linked to a DNA sequence if the promoter were capable of effecting transcription of that DNA sequence. In order to be "operably linked" it is not necessary that two sequences be immediately adjacent to one another. A nucleic acid molecule, such as DNA, is said to be "capable of expressing" a mRNA if it contains nucleotide sequences which contain transcriptional regulatory information and such sequences are "operably linked" to nucleotide sequences which encode the RNA. The precise nature of the regulatory regions needed for gene expression may vary from organism to organism, but in general include a promoter which directs the initiation of RNA transcription. Such regions may include those 5'-non-coding sequences involved with initiation of transcription such as the TATA box.

If desired, the non-coding region 3' to the gene sequence coding for the desired RNA product may be obtained. This region may be retained for its transcriptional termination regulatory sequences, such as those which provide for termination and polyadenylation. Thus, by retaining the 3'-region naturally contiguous to the coding sequence, the transcriptional termination signals may be provided. Where the transcriptional termination signals are not satisfactorily functional in the expression host cell, then a 3' region functional in the host cell may be substituted.

The promoter may be a "ubiquitous" promoter active in essentially all cells of the host organism, e.g., for mammals, the beta-actin promoter, or it may be a promoter whose expression is more or less specific to the target cells. Generally speaking, the latter is preferred. A promoter native to a gene which is naturally expressed in the target cell may be used for this purpose, e.g., the PEPCK (phosphoenol pyruvate carboxykinase) promoter for expression in mammalian liver cells. Other suitable promoters include albumin, metallothionein, surfactant, apoE, pyruvate kinase, LDL receptor HMG CoA reductase or any promoter which has been isolated, cloned and shown to have an appropriate pattern of tissue specific expression and regulation by factors (hormones, diet, heavy metals, etc.) required to control the transcription of the gene in the target tissue. In addition, a broad variety of viral promoters can be used; these include MMTV, SV-40 and CMV. An "expression vector" is a vector which (due to the presence of appropriate transcriptional and/or translational control sequences) is capable of expressing a DNA (or cDNA) molecule which has been cloned into the vector and of thereby producing an RNA or protein product. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, when a eukaryotic expression vector is employed, then the appropriate host cell would be any eukaryotic cell capable of expressing the cloned sequences.

In addition to or instead of an expressible gene, the nucleic acid may comprise sequences homologous to genetic material of the target cell, whereby it may insert itself ("integrate") into the genome by homologous recombination, thereby displacing a coding or control sequence of a gene, or deleting a gene altogether.

In another embodiment, the nucleic acid molecule is "antisense" to a genomic or other DNA sequence of the target organism (including viruses and other pathogens) or to a messenger RNA transcribed in cells of the organisms, which hybridizes sufficiently thereto to inhibit the transcription of the target genomic DNA or the translation of the target messenger RNA. The efficiency of such hybridization is a function of the length and structure of the hybridizing sequences. The longer the sequence and the closer the complementarily to perfection, the stronger the interaction. As the number of base pair mismatches increases, the hybridization efficiency will fall off. Furthermore, the GC content of the packaging sequence DNA or the antisense RNA will also affect the hybridization efficiency due to the additional hydrogen bond present in a GC base pair compared to an AT (or AU) base pair. Thus, a target sequence richer in GC content is preferable as a target.

It is desirable to avoid antisense sequences which would form secondary structure due to intramolecular hybridization, since this would render the antisense nucleic acid less active or inactive for its intended purpose. One of ordinary skill in the art will readily appreciate whether a sequence has a tendency to form a secondary structure. Secondary structures may be avoided by selecting a different target sequence.

An oligonucleotide, between about 15 and about 100 bases in length and complementary to the target sequence may be synthesized from natural mononucleosides or, alternatively, from mononucleosides having substitutions at the non-bridging phosphorous bound oxygens. A preferred analogue is a methylphosphonate analogue of the naturally occurring mononucleosides. More generally, the mononucleoside analogue is any analogue whose use results in oligonucleotides which have the advantages of (a) an improved ability to diffuse through cell membranes and/or (b) resistance to nuclease digestion within the body of a subject (Miller, P. S. et al., Biochemistry 20:1874–1880 (1981)). Such nucleoside analogues are well-known in the art. The nucleic acid molecule may be an analogue of DNA or RNA. The present invention is not limited to use of any particular DNA or RNA analogue, provided it is capable of fulfilling its therapeutic purpose, has adequate resistance to nucleases, and adequate bioavailability and cell take-up. DNA or RNA may be made more resistant to in vivo degradation by enzymes, e.g., nucleases, by modifying internucleoside linkages (e.g., methylphosphonates or phosphorothioates) or by incorporating modified nucleosides (e.g., 2'-O-methylribose or 1'-alpha-anomers). The entire nucleic acid molecule may be formed of such modified linkages, or only certain portions, such as the 5' and 3' ends, may be so affected, thereby providing resistance to exonucleases.

Nucleic acid molecules suitable for use in the present invention thus include but are not limited to dideoxyribonucleoside methylphosphonates, see Mill, et al., Biochemistry, 18:5134–43 (1979), oligodeoxynucleotide phosphorothioates, see Matsukura, et al., Proc. Nat. Acad. Sci., 84:7706–10 (1987), oligodeoxynucleotides covalently linked to an intercalating agent, see Zerial, et al., Nucleic Acids Res., 15:9909–19 (1987), oligodeoxynucleotide conjugated with poly(L-lysine), see Leonetti, et al., Gene, 72:32–33 (1988), and carbamate-linked oligomers assembled from ribose-derived subunits, see Summerton, J., Antisense Nucleic Acids Conference, 37:44 (New York 1989).

F. Pharmaceutical Compositions And Methods

The virally contained nucleic acid, operationally encoding a tethering protein such as LANA or EBNA1, may be admixed with a pharmaceutically acceptable excipient (i.e., carrier) for administration to a human or other animal subject. The administration may be by any suitable route of administration. The dosage form must be appropriate for that route. Suitable routes of administration and dosage forms include intravascular (injectable solution), subcutaneous (injectable solution, slow-release implant), topical (ointment, salve, cream), and oral (solution, tablet, capsule). With some routes of administration, the dosage form must be formulated to protect the conjugate from degradation, e.g., by inclusion of a protective coating or of a nuclease inhibitor.

The dosage may be determined by systematic testing of alternative doses, as is conventional in the art.

Rats (200–300 g) tolerate as much as 600 µg doses of DNA complex without any apparent ill effects on growth or health. Mice (25 g) have been injected with 150 µg of that DNA complex without any apparent problem.

In humans, a typical trial dose would be 60–120 mg of DNA this may be increased (or decreased) in a systematic manner, until an optimum dose is identified.

For short life span cells, e.g, macrophages, a typical dosing schedule might be one dose every two weeks. For long life span cells, e.g., hepatocytes, one dose every two months might be preferable.

Adjuvants may be used to decrease the size of the DNA complex (e.g., 2–10 mM MgCl), to increase its stability (e.g., sucrose, dextrose, glycerol), or to improve delivery efficiency (e.g, lysosomotropic agents such as chloroquine and monensine). The complexes may be enclosed in a liposome to protect them and to facilitate their entry into the target cell (by fusion of the liposome with the cell membrane).

For virally delivered therapeutics, aerosols may be employed. Additionally, the therapeutic viruses may be injected intravenously, subcutaneously, interperatinally or directly into the organ or tissue of choice.

3. Method Related to the Treatment of Viral Infections

The present invention contemplates compounds and methods for the treatment of viral infections. For example, it is contemplated that viral vectors can be produced that encode for tethering proteins (e.g. LANA and EBNA1) mutated to bind host histone H1 with greater avidity than wild type but not bind viral DNA binding sites. It is further contemplated that the binding of the mutant tethering protein to histone H1 of the host chromosomes would competitively or noncompetitively block the disease causing virus from binding to the host cell and thereby eliminate the persistence of the disease causing virus in the host cell. A virus could be constructed that replaced the native tethering protein with the mutant gof (gain-of-function) tethering protein. Such viral vectors would encoded mutant tethering protein that will block histone H1 sites thereby preventing infectious viral DNA from being replicated along with host DNA. After administration of the virus containing the mutant tethering protein, the patient would be monitored for progression of the disease.

Experimental

The following examples serve to illustrate certain preferred embodiments and aspects of the present invention and are not to be construed as limiting the scope thereof.

In the disclosure which follows, the following abbreviations apply: °C. (degrees Centigrade); g (gravitational field); vol (volume); w/v (weight to volume); v/v (volume to volume); BSA (bovine serum albumin); CTAB (cetyltrimethylammonium bromide); fmol (femtomole); FPLC (fast protein liquid chromatography); HEPES (N-[2-Hydroxyethyl]piperazine-N-[2'-ethanesulfonic acid]); HPLC (high pressure liquid chromatography); DTT (dithiothreitol); DMF (N,N dimethyl formamide); DNA (deoxyribonucleic acid); i.d. (internal diameter); p (plasmid); µl (microliters); ml (milliliters); µg (micrograms); pmoles (picomoles); mg (milligrams); MOPS (3-[N-Morpholino]propanesulfonic acid); M (molar); mM (milliMolar); µM (microMolar); nm (nanometers); kdal (kilodaltons); OD (optical density); EDTA (ethylene diamine tetra-acetic acid); FITC (fluorescein isothiocyanate); LC sulfo SPDP (LC sulfo-N-succinimidyl-3-(2-pyridyldithio)proprionate); SDS (sodium dodecyl sulfate); $NaPO_4$ (sodium phosphate); Tris (tris (hydroxymethyl)-aminomethane); PMSF (phenylmethylsulfonylfluoride); TBE (Tris-Borate-EDTA, e.g., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); Tween (polyoxyethylene-sorbitan); Boehringer Mannheim or BM (Boehringer Mannheim, Indianapolis, Ind.); New England Biolabs or NEB (New England Biolabs, Beverly, Mass.); Novagen (Novagen, Inc., Madison, Wis.); Pharmacia (Pharmacia Biotech Inc., Piscataway, N.J.); Perkin Elmer (Perkin Elmer, Norwalk, Conn.); Pierce (Pierce Chemical Co., Rockford, Ill.); Promega (Promega Corp., Madison, Wis.); Qiagen (Qiagen Inc., Chatsworth, Calif.); Stratagene (Stratagene Cloning Systems, La Jolla, Calif.); USB or U.S. Biochemical (U.S. Biochemical, Cleveland, Ohio).

Methods

Genomic and cDNA clones, cell culture, and transfection. Cosmid and Lambda clones spanning the KSHV genome (Z2, Z6, Z8 and L48, L54, L56, L72, respectively) were obtained from the AIDS Research and Reference Reagent Program (Russo, J. "Nuclotide sequence of the Kaposi sarcoma-associated herpesvirus (HHV8)" *Proc Natl Acad Sci* 93:14862–14867:1996). Orf 73 cDNA was obtained by polymerase chain reaction amplification of DNA using Vent DNA polymerase (NEB) from a body cavity lymphoma derived cell line (BC-1) with the following primers: 5'-GAGAATTCTTATGGCGCCCCCGGGAATG-3' (sense) (SEQ ID NO:5), 5'-GAGATATCCCTGTCATTTCCTGTGGAGA-3' (antisense) (SEQ ID NO:6). Fragments were purified, digested with EcoRI and EcoRV and cloned into a myc-tagged expression vector, pA3M (Aster, J. C., et al. "Oncogenic forms of NOTCH1 lacking either the primary binding site for RBP-Jkappa or nuclear localization sequences retain the abiltiy to associate with RBP-Jkappa and activate transcription" *J. Biol. Chem.* 272:11336–11343, 1997). BC-1, BC-3 (obtained from ATCC), and BJAB (obtained from Elliott Kieff) cells were grown in RPMI 1640 (Gibco), supplemented with 20% FCS (10% for BJAB), penicillin (25 U/ml), streptomycin (25 µg/ml), and gentamicin (10 µg/ml). 15 million cells were collected and transfected with 50 µg KSHV cosmid DNA (Z2 or Z8) and 50 µg LANA-myc plasmid cDNA (or myc vector alone) by electroporation (220 V, 975 µF). 18 hours after transfection, cells were collected for immunoFISH and western blot analysis.

FISH analysis. Metaphase chromosome spreads for FISH were prepared with standard protocols. Briefly, cells were metaphase arrested with colcemid (10 µg/ml, Gibco) for 1 hour at 37° C., then treated with 0.075 M KCl for 12 minutes at 37° C., followed by overnight fixation in fresh methanol/ acetic acid (3:1) at 4° C. Cells were spread on slides and allowed to age for no less than 72 hours. Hybridization was done overnight at 37° C. with a digoxigenin-labeled KSHV cosmid probe and then detected with rhodamine conjugated anti-digoxigenin antibodies, and counterstained with DAPI (4,6-diamidino-2 phenylindole).

Preparation of metaphase chromosomes for immunofluorescent analysis. Chromosome spreads for immunofluorescence were prepared as above except that fixation time was shortened to 1 hour to preserve chromosome-associated antigens. Slides were blocked in 20% normal goat serum for 30 minutes at room temperature, washed in PBS, and incubated in human serum reactive to LANA overnight at 4° C. Slides were again washed and then incubated in goat anti-human FITC secondary antibody (1:1000) for 1 hour at room temperature. Slides were washed, counterstained with DAPI, and coverslipped with antifade solution (2% n-propyl gallate in 70% glycerol) for fluorescence microscopy analysis.

In vitro DNA binding. Cosmid and lambda probes of KSHV DNA were radiolabeled with $^{32}$P-dCTP through a standard nick translation protocol (Sambrook, J., et al. "Molecular Cloning: A Laboratory Manual" *Cold Spring Harbor Laboratory Press*, ed. 2, 1997, pp.3.6–3.12) and separated from unincorporated label with NucTrap probe purification columns (Stratagene). $^{35}$S-methionine labeled LANA-myc protein was generated by in vitro translation of a LANA-myc CDNA with rabbit reticulocyte lysate (Promega) as per manufacturer's suggestions. 3 µl of labeled protein was incubated with 3 µl labeled KSHV probe at 4° C. for 45 minutes in 50 µl EMSA buffer. Simultaneously, 25 µl Protein G-sepharose beads were incubated with 50 µl monoclonal anti-myc antibody (supernatant from 9E10 hybridoma cells) in 350 µl binding buffer rotating at 4° C. for 45 minutes. Bound DNA protein complexes were added to prebound Ab-Protein G-sepharose complexes and incubated for 45 minutes, rotating at 4° C. Complexes were then collected by centrifugation at 15,000 rpm for 1 minute at 4° C. in a microcentrifuge. Precipitates were washed twice by removal of supernatant, resuspension in 200 µl binding buffer, and recentrifugation. Supernatants from washes were pooled and counted in a liquid scintillation counter as were the corresponding pellets. DNA bound to LANA protein (correcting for amount of protein) was then calculated with the following formula: ($^{32}$P pellet/$^{35}$S pellet)/($^{32}$P supernatant/$^{35}$S supernatant).

Preparation of metaphase chromosomes for ImmunoFISH double labeling. Metaphase chromosome spreads for ImmunoFISH colocalization were prepared as above with a 1 hour fixation period to preserve chromosome-associated antigens. Hybridization was done overnight at 37° C. with a biotinylated KSHV cosmid or lambda probe and then detected with a direct tyramide-rhodamine signal amplification system (NEN Life Sciences), according to manufacturer's suggestions. After repeated washes, slides were subjected to the immunofluorescence protocol as above. Slides were washed, counterstained with DAPI, and coverslipped with antifade for fluorescence microscopy analysis.

Immunoprecipitation and in vitro binding. One hundred million BC-1, BC-3, or BJAB cells were lysed in RIPA buffer and pre-cleared by incubation with protein A alone. Immunoprecipitates were generated with monoclonal histone H1 antibodies (2 µg/ml-Upstate Biotechnology), washed four times in RIPA buffer (1% Nonidet P-40, 0.5% deoxycholate, 0.1% SDS and protease inhibitors), then fractionated by SDS-PAGE and transferred to nitrocellulose membranes. Western blots were performed with human serum reactive to LANA at a 1:500 dilution and standard chemiluminescence detection protocols. For in vitro binding experiments, 50 µg of crude histones (type II-A, Sigma) were incubated with 20 µl of in vitro translated LANA-myc fusion protein for 3 hours at 4° C. Complexes were precipitated by the addition of anti-myc antibodies and protein G-Sepharose beads followed by centrifugation. Immunoprecipitates were fractionated by SDS-PAGE and transferred to nitrocellulose membranes for western blot analysis with monoclonal histone H1 antibodies.

Immunofluorescent colocalization. For colocalization of LANA and histone H1, slides were blocked in 1% BSA for 30 minutes at room temperature, then incubated in 20 µg/ml monoclonal anti-histone H1 (Upstate Biotechnology) overnight at 4° C. Slides were washed and then incubated in anti-LANA serum overnight at 4° C. After more PBS washes, slides were incubated in goat anti-human FITC (1:1000) and donkey anti-mouse rhodamine (1:100) for 1 hour at room temperature. Slides were washed in PBS and coverslipped with antifade for analysis on an Olympus AX70 fluorescent microscope.

Experiment 1

LANA and KSHV episomes localize similarly to host chromatin in KSHV infected cells. To determine if KSHV achieves latency by integrating to host DNA, we conducted fluorescent in-situ hybridization (FISH) studies with several viral cosmid probes on metaphase chromosomes prepared from a KSHV positive/EBV negative cell line (BC-3) derived from a body cavity lymphoma as well as a KSHV negative B cell line (BJAB). While viral DNA was not detected in the symmetrical pattern achieved by replication of a chromatid to which virus has integrated, it was consistently detected in a seemingly random association with host chromosomes (FIG. 1a). Furthermore, when similar chromosome spreads derived from the same KSHV positive cells were probed with a human serum that specifically recognizes LANA (FIG. 1b), we demonstrated that LANA localized to the host chromosomes in a pattern strikingly similar to that of KSHV specific DNA hybridization in FIG. 1a. FIG. 1c shows a non-specific control. This chromosome associated pattern of immunofluorescence was not evident in metaphase spreads probed with normal human serum adsorbed against antigens from an EBV negative cell line, BJAB, as well as an EBV positive line, B958 (data not shown), suggesting that the signal is specific for LANA and not due to a nonspecific signal from the polyclonal human serum. Therefore our results indicated that LANA has the ability to bind sequences on the KSHV genome.

Experiment 2

LANA displays preferential binding to different regions of KSHV DNA in vitro. To ascertain if LANA had the capacity to bind specific sequences in KSHV DNA, $^{32}$P-dCTP radiolabeled probes spanning the viral genome (FIG. 2b) were incubated with in vitro translated $^3$S-methionine labeled LANA-myc fusion protein, followed by immunoprecipitation with anti-myc antibodies. To detect probes specifically bound to LANA, immunoprecipitates were quantified by liquid scintillation counting. Binding of LANA to DNA was expressed as a percentage of total probe that coimmunoprecipitated with LANA-myc. The results of this experiment, shown in FIG. 2a, demonstrated that LANA most preferentially bound a region of the KSHV genome referred to as Z2, located at approximately 127–140 kb on the right end of the viral genome (Russo, J. "Nucleotide sequence of the Kaposi sarcoma-associated herpesvirus (HHV8)" *PNAS* 93:14862–14867, 1996). FIG. 2a is a representative of three separate experiments in which Z2 bound to LANA-myc more favorably than other regions of the KSHV genome. Region Z6 at the left end of the viral genome and L48 bound less preferentially to the immunoprecipitated LANA. Similar to EBNA 1, an EBV protein important for maintenance of EBV episomes (Mackey, D. and Sugden, B. "Studies on the mechanism of DNA linking by Epstein-Barr virus nuclear antigen" *J. Biol. Chem.* 272:29873–29879, 1997; Hal Jones, C., et al. "Interaction of the lymphocyte-derived Epstein-Barr virus nuclear antigen EBNA-1 with its DNA-binding sites" *J. Virol.* 63:101–110, 1989; Yates, J. L., et al. "Stable replication of plasmids derived from Epstein-Barr virus in various mammalian cells" *Nature* 313:812–815, 1985; Rawlins, D. R., et al. "Sequence-specific DNA binding of the Epstein-Barr virus nuclear antigen (EBNA-1) to clustered sites in the plasmid maintenance region" *Cell* 42:859–868, 1985; Ambinder, R. F., et al. "Definition of the sequence requirements for binding of the EBNA-1 protein to its palindromic target sites in Epstein-Barr virus DNA" *J. Virol.* 64:2369–2379, 1990), LANA may bind several different sites in the KSHV genome, suggesting multiple fimctional roles of LANA in KSHV latent infection.

Experiment 3

Figure 3:
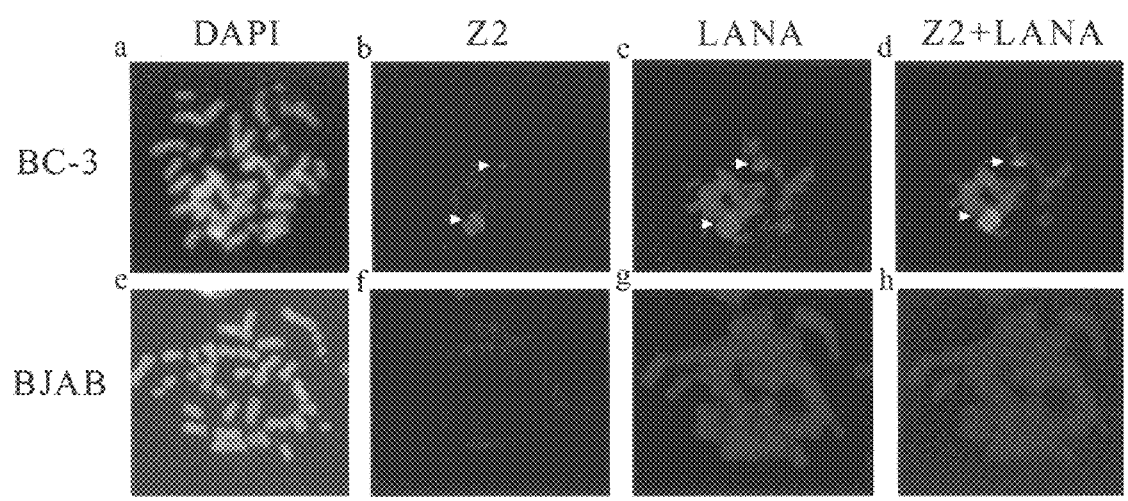
FIG. 3. KSHV DNA colocalizes with LANA to host chromosomes in BC-3 cells but not the KSHV negative control BJAB cells.

LANA and KSHV DNA colocalize to metaphase chromosomes in KSHV infected cells. To determine if LANA colocalized with KSHV DNA, chromosome spreads were generated from cells prepared by fixing for only one hour in an effort to retain chromosome-associated antigens that would be lost by the typical overnight fixation used in standard FISH protocols as shown in FIG. 1a. These spreads were probed with KSHV DNA and amplified via a tyramide based fluorochrome deposition (NEN-Lifesciences) for increased sensitivity, followed immediately by anti-LANA immunofluorescence in an effort to colocalize viral DNA and LANA protein at host chromosomes. When both signals from the KSHV probe and the anti-LANA antibody were superimposed it became evident that both signals were colocalized to the chromosomes in BC-3 (FIG. 3d) but not BJAB cells (FIG. 3h).

Experiment 4

Figure 4:
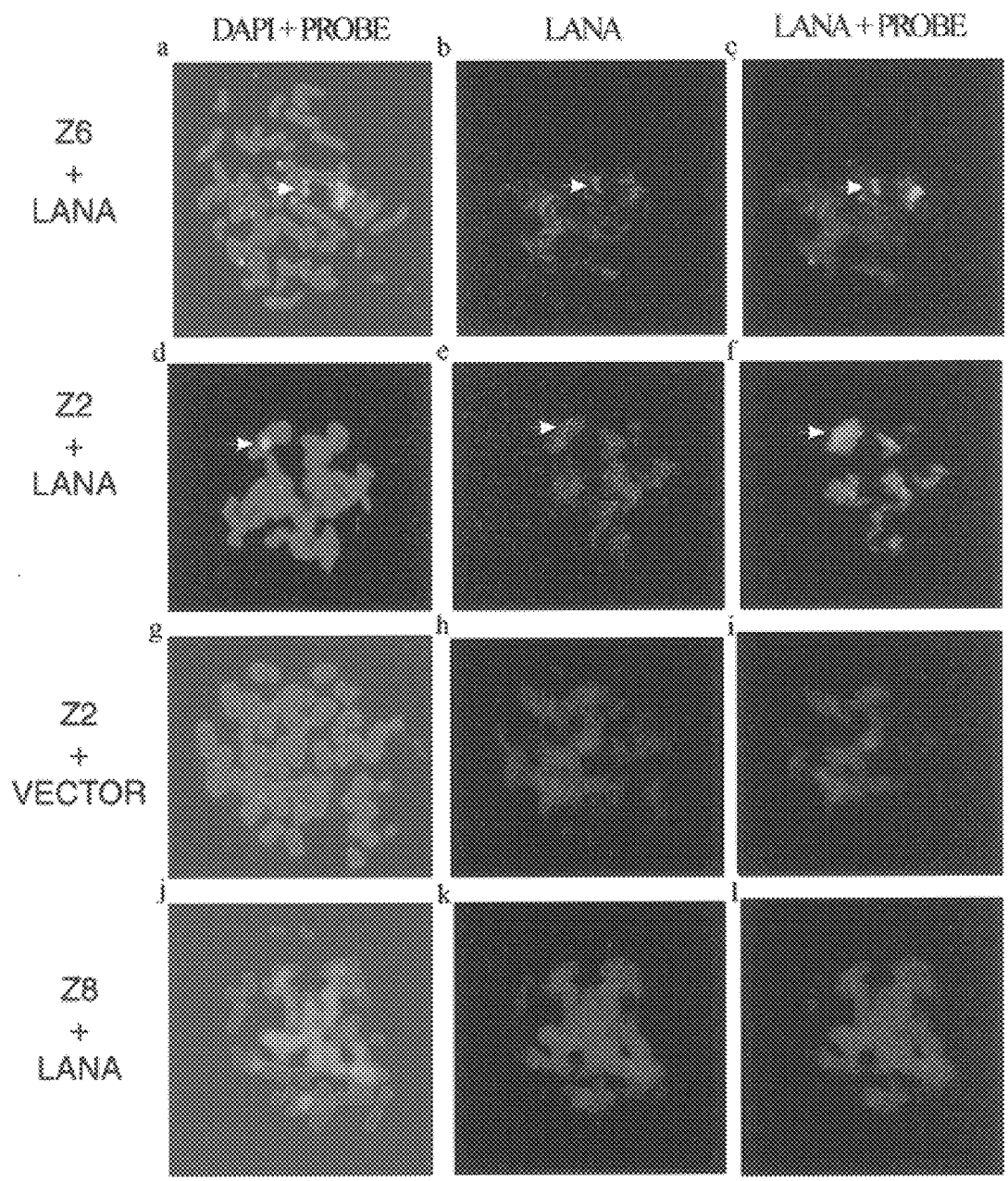
FIG. 4. Cis-acting elements within the Z6 and Z2 regions of the KSHV genome and LANA are sufficient to confer colocalization of KSHV viral DNA and LANA to host chromosomes.

Cis-acting DNA elements in Z2 plus LANA are sufficient for chromosomal localization in transfected cells. These data provide the basis for further experiments in which we tested the hypothesis that Z2, through its preferential binding to LANA, may contain cis-acting elements that can cooperate with LANA to confer chromosome localization of the KSHV genome. BJAB cells were cotransfected with equivalent amounts of Z2 or Z8 along with an expression construct of a LANA-myc fusion protein under the control of the CMV IE promoter. ImmunoFISH was then carried out on these cells, using the appropriate cosmid probe followed by immunofluorescence with anti-LANA antibodies. Analysis of these transfected cells revealed the colocalization of Z2, but not Z8 viral DNA with LANA to the host chromosomes (FIGS. 4a–c,g–i). Furthermore, this colocalization was dependent on the presence of LANA protein as Z2 did not localize to host chromosomes when cotransfected with empty myc vector (FIGS. 4d–f). Interestingly, chromosomes from cells transfected with Z8 and LANA-myc could not be labeled for either Z8 DNA or LANA protein (FIG. 4g–I), suggesting that the presence of specific viral DNA may be necessary for the stabilization of LANA's interaction with host chromatin. These data indicate that LANA and cis-acting elements in Z2 are sufficient for chromosome localization of KSHV DNA. Additionally, similar experiments with Z6 demonstrated that Z6 can also colocalize with LANA to the host chromosomes (unpublished observations-MAC and ESR). Furthermore, our binding studies indicate that other regions of the KSHV genome (Z6 and L48) may contain other cis-acting elements through which LANA may link the KSHV genome to host chromosomes.

Experiment 5

Figure 5:
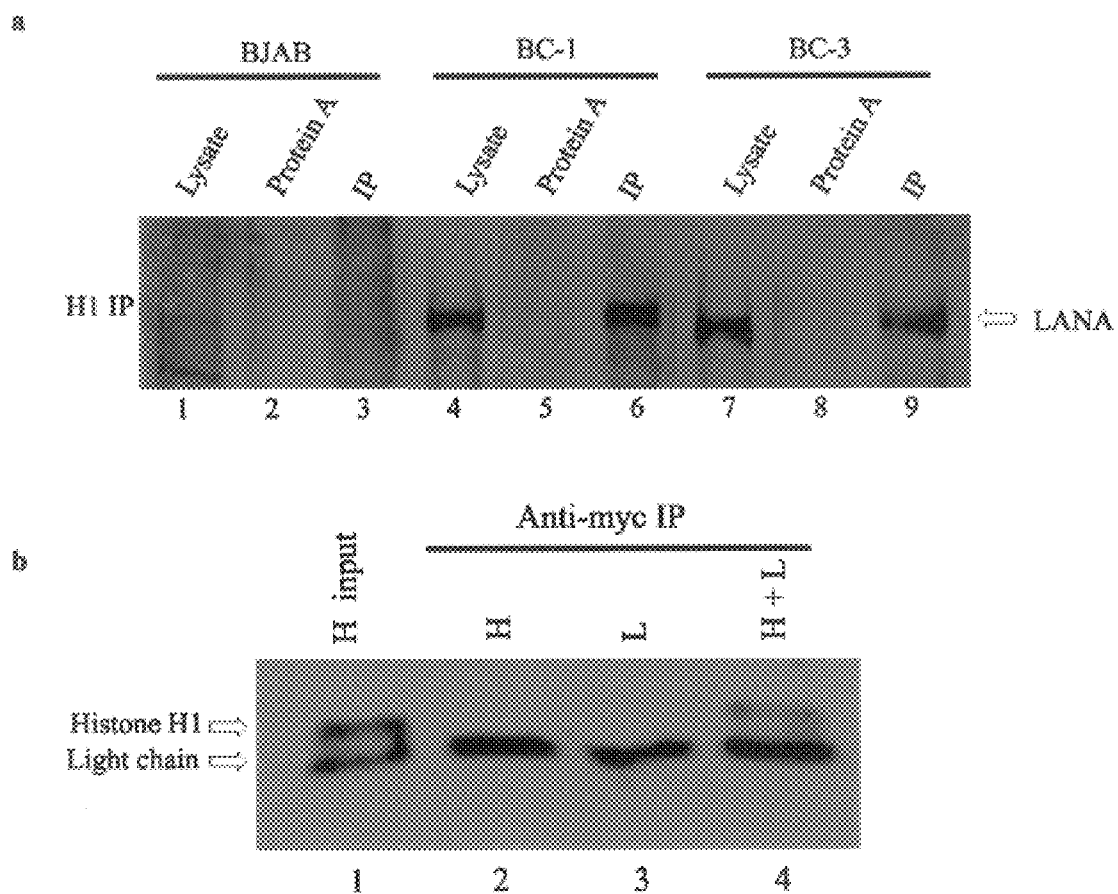
FIG. 5. The KSHV encoded LANA protein interacts with nucleosomal histone H1 protein.
Figure 5C:
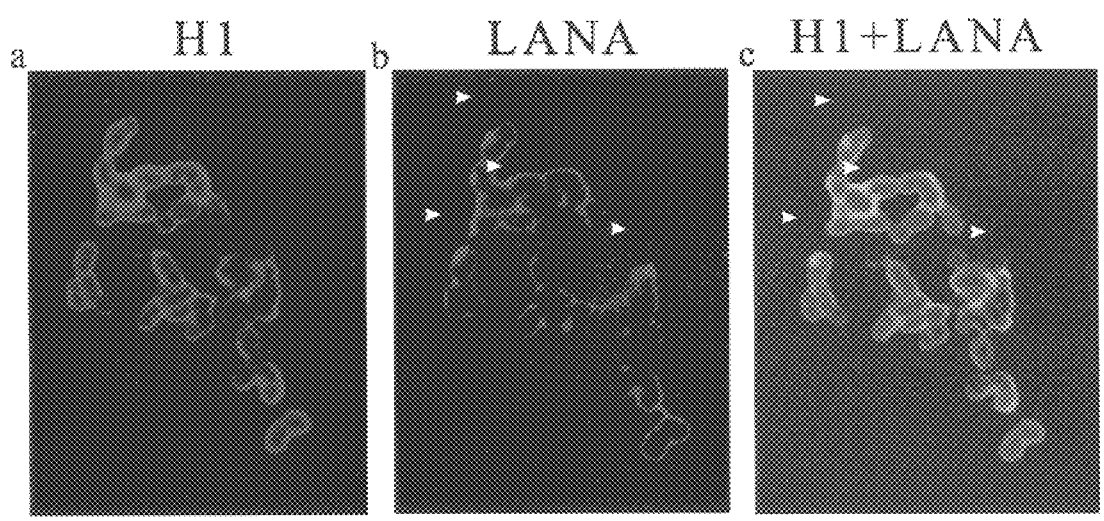

LANA interacts with the nucleosome-associated histone H1 protein. The results of these experiments prompted us to hypothesize that LANA tethers KSHV episomes at Z2 to host chromosomes potentially through interaction with chromosomal proteins. Therefore, coimmunoprecipitation experiments were conducted to determine if LANA specifically interacts with nucleosome-associated histone proteins that could allow for a mechanism by which the KSHV genome is tethered to host chromosomes. Immunoprecipitates were generated from BC-1, BC-3, and BJAB cells with antibodies against histone H1 and separated by SDS-PAGE. Western blot analysis of anti-histone H1 immunoprecipitates using anti-LANA human serum (FIG. 5a) revealed a 222–234 kDa band comigrating in lysate and immunoprecipitation lanes in BC-1 and BC-3 but not in BJAB cells. A similar result was generated from the reciprocal experiment. Crude histones were incubated with in vitro translated LANA-myc fusion protein, then immunoprecipitated with anti-myc antibodies, and fractionated by SDS-PAGE. Anti-histone H1 western blot analysis of these immunoprecipitates revealed a 33 kD comigrating with an identical band in the histone input lane, but not in control lanes (FIG. 5b). Additionally, through immunofluorescence analysis using antibodies against histone H1 and LANA we have demonstrated that histone H1 and LANA colocalize to metaphase chromosomes in BC-3 cells (FIG. 5c). Given the acidic nature of the LANA protein, it was possible that LANA may also interact with other chromosomal proteins such as histones H3 and H4, however experiments conducted with specific antibodies to these nucleosomal antigens (Upstate Biotechnologies) did not yield positive results (data not shown).

Experiment 6

Localization of three specific LANA binding regions (LBR) within the KSHV genome. In order to screen for specific regions of KSHV DNA that bind DNA, Z2, Z6 and Z8 were pooled and incubated with in vitro translated LANA-myc and the immunoprecipitated with monoclonal anti-myc antibodies. These precipitates were washed and then digested with frequent cutter Sau3A1. These digests were then extracted with phenol and chloroform. Sau3A1 fragments that were protected by interaction with LANA were precipitated from the aqueous phase and ligated into the BamH1 site in the MCS of pHbluescript. This ligation was then transformed into competent *E. coli* cells and plated onto LB-ampicillin. Single colonies were picked for plasmid DNA preparation and insert sequencing. The three LBR sites, labeled 1, 2 and 3, represent inserts whose sequences showed up redundantly in this experiment and contain sequence similarities which may reflect the presence of a LANA consensus site. These regions are located at approximately 22–27 kb, 109–111 kb, and 127–132 kb and are shown schematically in FIG. 6.

Experiment 7

Figure 7:
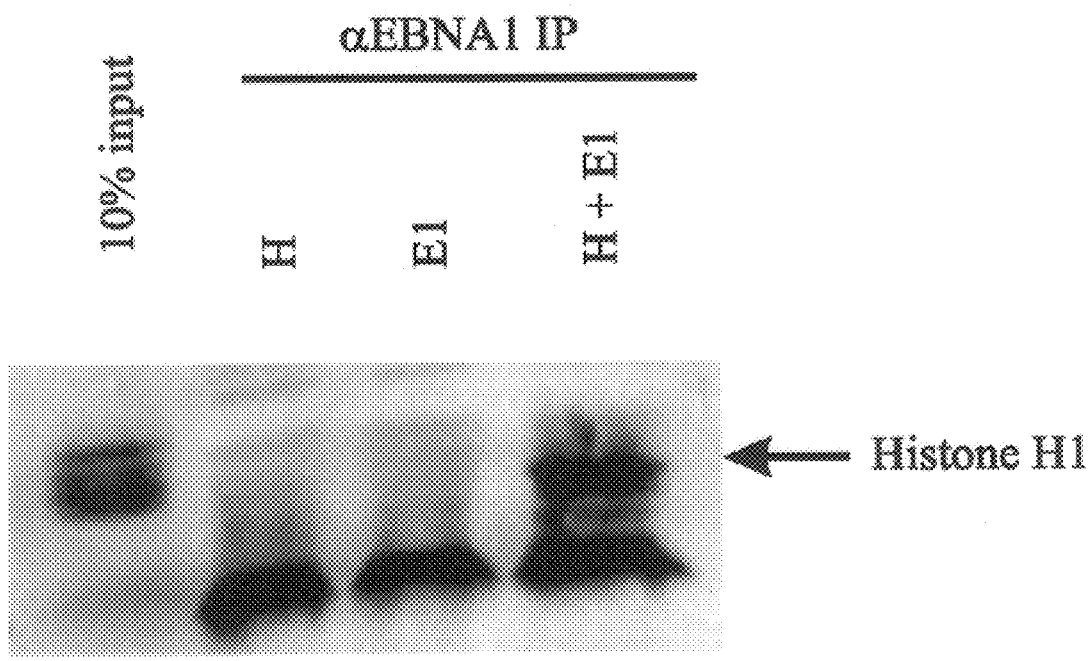
FIG. 7. EBNA1 interacts with histone H1 in vitro. H—crude histones alone; E1—in vitro translated EBNA1 alone; H+E1—crude histones plus in vitro translated EBNA1.

EBNA1 interacts with histone H1 in vitro. In another gammaherpesvirus, Epstein-Barr virus (EBV), the protein which is known to be important for episomal maintenance (EBNA1) also interacts with histone H1, both in vitro and in EBV infected lymphoblastoid cell lines, suggesting that chromosomal tethering of viral episomes may be a conserved strategy for viral latency. 250 micrograms of crude histones were incubated for 1 hour at 4 degrees centigrade with 20 microliters of in vitro translated EBNA1. Human serum reactive to EBNA1 was added and incubated for one hour at 4 degrees. Immunoprecipitates were generated by centrifugation after one hour incubation with Protein A-sepharose beads. After repeated washing, these precipitates were fractionated by SDS-PAGE, transferred to nitrocellulose and probed with a monoclonal anti-histone H1 antibody (FIG. 7).

Experiment 8

Figure 8:
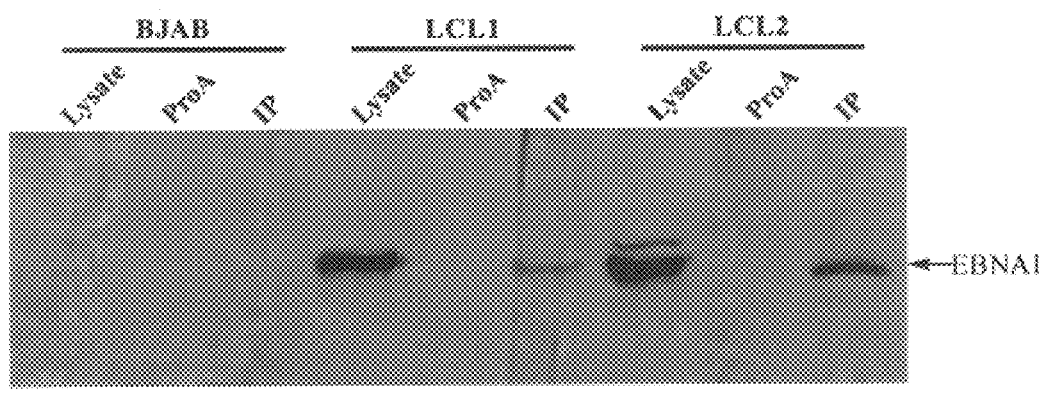
FIG. 8. EBV encoded EBNA1 interacts with histone H1 in EBV infected LCL1 cells. L—10% lysate not subject to IP; ProA—Protein A beads preclear; histone H1 IP—immunoprecipitate generated with monoclonal anti-histone H1 antibody. Non-viral background band appearing in BJAB IP due to nonspecific reaction of polyvalent human sera with cellular antigens.

EBV encoded EBNA 1 interacts with histone 1 in EBV infected LCL1 cells. 50 million BJAB (non EBV infected) and LCL1 cells were lysed in RIPA buffer and incubated with Protein A-sepharose beads for 1 hour and precipitated to preclear the lysate of nonspecific interactions (ProA lanes above). After preclear, the lysates were incubated overnight at 4 degrees with a monoclonal anti-histone H1 antibody (Upstate Biotechnologies). Immunoprecipitates were generated by the addition of Protein A-sepharose beads. These precipitates were then SDS-PAGE fractionated, transferred to nitrocellulose and probed with a human serum reactive to EBNA1 (FIG. 8).

From the above it is clear that the present invention provides novel compounds and methods for the screening of agents that are agonistic or antagonistic for the binding of viral proteins to host cells. Additionally, the present invention provides novel compounds and methods useful for gene therapy applications.

What is claimed is:

1. A cell-free method for screening compounds, said method comprising:

a) providing; i) a viral nucleic acid binding protein; ii) histone H1; and iii) a compound suspected of modulating the interaction of said binding protein with histone H1;

b) admixing said binding protein, said histone H1 and said compound to make a cell-free mixture, and;

c) assaying for the binding of said binding protein with said histone H1, thereby screening said compound for interaction.

2. The method of claim 1 wherein said viral nucler acid binding protein is selected from a group consisting of LANA and EBNA1.

3. A cell-free composition comprising viral nucleic acid tethered to histone H1 protein by a viral nucleic acid-binding protein.

* * * * *

SEQUENCE LISTING

<160> NUMBER OF SEQ ID NOS: 6

<210> SEQ ID NO 1
<211> LENGTH: 3489
<212> TYPE: DNA
<213> ORGANISM: Kaposi's sarcoma-associated herpesvirus

<400> SEQUENCE: 1

| | | | | | |
|---|---|---|---|---|---|
| atggcgcccc | cgggaatgcg | cctgaggtcg | ggacggagca | ccggcgcgcc | cttaacgaga | 60 |
| ggaagttgta | ggaaacgaaa | caggtctccg | gaaagatgtg | accttggcga | tgacctacat | 120 |
| ctacaaccgc | gaaggaagca | tgtcgccgac | tccatcgacg | gccgggaatg | tggaccccac | 180 |
| accttgccta | tacctggaag | tcccacagtg | ttcacatccg | ggctgccagc | atttgtgtct | 240 |
| agtcctactt | taccggtggc | tcccattcct | tcacccgctc | ccgcaacacc | tttacctcca | 300 |
| ccggcactct | taccccccgt | aaccacgtct | tcctccccaa | tccctccatc | ccatcctgtg | 360 |
| tctccgggga | ccacggatac | tcattctcca | tctcctgcat | tgccacccac | gcagtctcca | 420 |
| gagtcttctc | aaaggccacc | gctttcaagt | cctacaggaa | ggccagactc | ttcaacacct | 480 |
| atgcgtccgc | caccctcgca | gcagactaca | cctccacact | cacccacgac | tcctccaccc | 540 |
| gagcctccct | ccaagtcgtc | accagactct | ttagctccgt | ctaccctgcg | tagcctgaga | 600 |
| aaaagaaggc | tatcgtcccc | ccaaggtccc | tctacactaa | acccaatatg | tcagtcgccc | 660 |
| ccagtctctc | cccctagatg | tgacttcgcc | aaccgtagtg | tgtacccccc | atgggccaca | 720 |
| gagtccccga | tctacgtggg | atcatccagc | gatggcgata | ctccgccacg | ccaaccgcct | 780 |
| acatctccca | tctccatagg | atcatcatcc | ccgtctgagg | gatcctgggg | tgatgacaca | 840 |
| gccatgttgg | tgctccttgc | ggagattgca | gaagaagcat | ccaagaatga | aaaagaatgt | 900 |
| tccgaaaata | atcaggctgg | cgaggataat | ggggacaacg | agattagcaa | ggaaagtcag | 960 |
| gttgacaagg | atgacaatga | caataaggat | gatgaggagg | agcaggagac | agatgaggag | 1020 |
| gacgaggagg | atgacgagga | ggatgacgag | gaggatgacg | aggaggatga | cgaggaggat | 1080 |
| gacgaggagg | atgacgagga | ggatgacgag | gaggatgacg | aggaggatga | cgaggaggat | 1140 |
| gacgaggagg | atgacgagga | ggaggacgag | gaggaggacg | aggaggagga | cgaggaggag | 1200 |
| gaggacgagg | aggatgacga | tgatgaggac | aatgaggacg | aggaggatga | cgaggaggag | 1260 |
| gacaagaagg | aggacgagga | ggacgggggc | gatggaaaca | aaacgttgag | catccaaagt | 1320 |

-continued

| | |
|---|---|
| tcacaacagc agcaggagcc acaacagcag gagccacagc agcaggagcc acagcagcag | 1380 |
| gagcccctgc aggagccaca acagcaggag ccacagcagc aggagccaca gcagcaggag | 1440 |
| cccctgcagg agccacaaca gcaggagcca cagcagcagg agcccctgca ggagccacaa | 1500 |
| cagcaggagc acaacagca ggagccacag cagcaggagc cacagcagca ggagccacag | 1560 |
| cagcaggagc cacagcagca ggagccacag cagcaggagc cacagcagca ggagccacag | 1620 |
| cagcaggagc cacagcagca ggagccacag cagcgggagc cacagcagcg ggagccccag | 1680 |
| cagcgggagc cacagcagcg ggagccacag cagcgggagc cacagcagcg ggagccacag | 1740 |
| cagcgggagc cacagcagcg ggagccacag cagcgggagc cacagcagca ggatgagcag | 1800 |
| cagcaggatg agcagcagca ggatgagcag cagcaggatg agcagcagca ggatgagcag | 1860 |
| cagcaggatg agcagcagca ggatgagcag cagcaggatg agcagcagca ggatgagcag | 1920 |
| cagcaggatg agcagcagca ggatgagcag cagcaggatg agcagcagca ggatgagcag | 1980 |
| cagcaggatg agcagcagca ggatgagcag cagcaggatg agcagcagca ggatgagcag | 2040 |
| cagcaggatg agcagcagca ggatgagcag cagcaggatg agcagcagca ggatgagcag | 2100 |
| gagcagcagg atgagcagga gcagcaggat gagcaggagc agcaggatga gcagcagcag | 2160 |
| gatgagcagc agcagcagga tgagcagcag cagcaggatg agcagcagca gcaggatgag | 2220 |
| cagcagcagc aggatgagca gcagcagcag gatgaacagg agcagcagga ggagcaggag | 2280 |
| cagcaggagg agcaggagca ggagttagag gagcaggagc aggagttaga ggatcaggag | 2340 |
| caggagttag aggagcagga gcaggagtta gaggagcagg agcaggagtt agaggagcag | 2400 |
| gagcaggagt tagaggagca ggagcaggag ttagaggagc aggagcagga gttagaggag | 2460 |
| caggagcagg agttagagga gcaggagcag gagttagagg agcaggagca ggagttagag | 2520 |
| gagcaggagg tggaagagca agagcaggag gtggaagagc aagagcagga gcaggaagag | 2580 |
| caggaattag aggaggtgga ggagcaagag caggagcagg aggagcagga ggagcaggag | 2640 |
| ttagaggagg tggaagagca ggaagagcag gagttagagg aggtggaaga gcaggaagag | 2700 |
| caggagttag aggaggtgga agagcaggag cagcaggagt tagaggaggt ggaagagcag | 2760 |
| gagcagcagg gggtggaaca gcaggagcag gagacggtgg aagagcccat aatcttgcac | 2820 |
| gggtcgtcat ccgaggacga aatggaagtg gattaccctg ttgttagcac acatgaacaa | 2880 |
| attgccagta gcccaccagg agataataca ccagacgatg acccacaacc tggcccatct | 2940 |
| cgcgaatacc gctatgtact cagaacatca ccaccccaca gacctggagt tcgtatgagg | 3000 |
| cgcgttccag ttacccaccc aaaaaagcca catccaagat accaacaacc accggtccct | 3060 |
| tacagacaga tagatgattg tcctgcgaaa gctaggccac aacacatctt ttatagacgc | 3120 |
| ttttttggga aaggatggaag acgagatcca aagtgtcaat ggaagtttgc agtgattttt | 3180 |
| tggggcaatg acccatacgg acttaaaaaa ttatctcagg ccttccagtt tggaggagta | 3240 |
| aaggcaggcc ccgtgtcctg cttgccccac cctggaccag accagtcgcc cataacttat | 3300 |
| tgtgtatatg tgtattgtca gaacaaagac acaagtaaga aagtacaaat ggcccgccta | 3360 |
| gcctgggaag ctagtcaccc cctggcagga aacctacaat cttccatagt taagtttaaa | 3420 |
| aagcccctgc cattaaccca gccaggggaa aaccaaggtc ctgggactc tccacaggaa | 3480 |
| atgacataa | 3489 |

<210> SEQ ID NO 2
<211> LENGTH: 1162
<212> TYPE: PRT
<213> ORGANISM: Kaposi's sarcoma-associated herpesvirus -continued

```
<400> SEQUENCE: 2

Met Ala Pro Pro Gly Met Arg Leu Arg Ser Gly Arg Ser Thr Gly Ala
 1               5                  10                  15

Pro Leu Thr Arg Gly Ser Cys Arg Lys Arg Asn Arg Ser Pro Glu Arg
             20                  25                  30

Cys Asp Leu Gly Asp Asp Leu His Leu Gln Pro Arg Arg Lys His Val
         35                  40                  45

Ala Asp Ser Ile Asp Gly Arg Glu Cys Gly Pro His Thr Leu Pro Ile
     50                  55                  60

Pro Gly Ser Pro Thr Val Phe Thr Ser Gly Leu Pro Ala Phe Val Ser
 65                  70                  75                  80

Ser Pro Thr Leu Pro Val Ala Pro Ile Pro Ser Pro Ala Pro Ala Thr
                 85                  90                  95

Pro Leu Pro Pro Ala Leu Leu Pro Pro Val Thr Thr Ser Ser Ser
            100                 105                 110

Pro Ile Pro Pro Ser His Pro Val Ser Pro Gly Thr Thr Asp Thr His
            115                 120                 125

Ser Pro Ser Pro Ala Leu Pro Pro Thr Gln Ser Pro Glu Ser Ser Gln
        130                 135                 140

Arg Pro Pro Leu Ser Ser Pro Thr Gly Arg Pro Asp Ser Ser Thr Pro
145                 150                 155                 160

Met Arg Pro Pro Ser Gln Gln Thr Thr Pro Pro His Ser Pro Thr
                165                 170                 175

Thr Pro Pro Pro Glu Pro Pro Ser Lys Ser Ser Pro Asp Ser Leu Ala
                180                 185                 190

Pro Ser Thr Leu Arg Ser Leu Arg Lys Arg Leu Ser Ser Pro Gln
            195                 200                 205

Gly Pro Ser Thr Leu Asn Pro Ile Cys Gln Ser Pro Pro Val Ser Pro
        210                 215                 220

Pro Arg Cys Asp Phe Ala Asn Arg Ser Val Tyr Pro Pro Trp Ala Thr
225                 230                 235                 240

Glu Ser Pro Ile Tyr Val Gly Ser Ser Ser Asp Gly Asp Thr Pro Pro
                245                 250                 255

Arg Gln Pro Pro Thr Ser Pro Ile Ser Ile Gly Ser Ser Ser Pro Ser
            260                 265                 270

Glu Gly Ser Trp Gly Asp Asp Thr Ala Met Leu Val Leu Leu Ala Glu
        275                 280                 285

Ile Ala Glu Glu Ala Ser Lys Asn Glu Lys Glu Cys Ser Glu Asn Asn
290                 295                 300

Gln Ala Gly Glu Asp Asn Gly Asp Asn Glu Ile Ser Lys Glu Ser Gln
                305                 310                 315                 320

Val Asp Lys Asp Asp Asn Asp Asn Lys Asp Asp Glu Glu Gln Glu
            325                 330                 335

Thr Asp Glu Glu Asp Glu Glu Asp Glu Glu Asp Asp Glu Glu Asp
                340                 345                 350

Asp Glu Glu Asp Asp Glu Glu Asp Glu Glu Asp Glu Glu Asp
            355                 360                 365

Asp Glu Glu Asp Glu Glu Asp Asp Glu Glu Asp Asp Glu Glu Asp
            370                 375                 380

Asp Glu Glu Glu Asp Glu Glu Glu Asp Glu Glu Asp Glu Glu Glu
385                 390                 395                 400

Glu Asp Glu Glu Asp Asp Asp Glu Asp Asn Glu Asp Glu Glu Asp
                405                 410                 415
```

-continued

```
Asp Glu Glu Glu Asp Lys Lys Glu Asp Glu Asp Gly Gly Asp Gly
            420                 425                 430

Asn Lys Thr Leu Ser Ile Gln Ser Ser Gln Gln Gln Gln Glu Pro Gln
            435                 440                 445

Gln Gln Glu Pro Gln Gln Gln Glu Pro Gln Gln Gln Glu Pro Leu Gln
            450                 455                 460

Glu Pro Gln Gln Glu Pro Gln Gln Gln Glu Pro Gln Gln Gln Glu
465                 470                 475                 480

Pro Leu Gln Glu Pro Gln Gln Glu Pro Gln Gln Gln Glu Pro Leu
                    485                 490                 495

Gln Glu Pro Gln Gln Glu Pro Gln Gln Glu Pro Gln Gln Gln
            500                 505                 510

Glu Pro Gln Gln Glu Pro Gln Gln Glu Pro Gln Gln Glu
            515                 520                 525

Pro Gln Gln Gln Glu Pro Gln Gln Glu Pro Gln Gln Glu Pro
            530                 535                 540

Gln Gln Gln Glu Pro Gln Gln Arg Glu Pro Gln Gln Arg Glu Pro Gln
545                 550                 555                 560

Gln Arg Glu Pro Gln Gln Arg Glu Pro Gln Gln Arg Glu Pro Gln Gln
            565                 570                 575

Arg Glu Pro Gln Gln Arg Glu Pro Gln Gln Arg Glu Pro Gln Gln Arg
            580                 585                 590

Glu Pro Gln Gln Asp Glu Gln Gln Asp Glu Gln Gln Asp
            595                 600                 605

Glu Gln Gln Gln Asp Glu Gln Gln Gln Asp Glu Gln Gln Gln Asp Glu
            610                 615                 620

Gln Gln Gln Asp Glu Gln Gln Gln Asp Glu Gln Gln Gln Asp Glu Gln
625                 630                 635                 640

Gln Gln Asp Glu Gln Gln Gln Asp Glu Gln Gln Gln Asp Glu Gln Gln
            645                 650                 655

Gln Asp Glu Gln Gln Gln Asp Glu Gln Gln Gln Asp Glu Gln Gln Gln
            660                 665                 670

Asp Glu Gln Gln Gln Asp Glu Gln Gln Gln Asp Glu Gln Gln Gln Asp
            675                 680                 685

Glu Gln Gln Gln Asp Glu Gln Gln Gln Asp Glu Gln Gln Gln Asp
            690                 695                 700

Glu Gln Glu Gln Gln Asp Glu Gln Gln Gln Asp Glu Gln Gln Gln
705                 710                 715                 720

Asp Glu Gln Gln Gln Asp Glu Gln Gln Gln Asp Glu Gln Gln
            725                 730                 735

Gln Gln Asp Glu Gln Gln Gln Gln Asp Glu Gln Gln Gln Gln Asp Glu
            740                 745                 750

Gln Glu Gln Gln Glu Gln Glu Gln Gln Glu Gln Glu Gln Glu
            755                 760                 765

Leu Glu Glu Gln Glu Gln Glu Leu Glu Asp Gln Glu Gln Glu Leu Glu
            770                 775                 780

Glu Gln Glu Gln Glu Leu Glu Gln Glu Gln Glu Leu Glu Glu Gln
785                 790                 795                 800

Glu Gln Glu Leu Glu Glu Gln Glu Gln Glu Leu Glu Glu Gln Glu Gln
            805                 810                 815

Glu Leu Glu Glu Gln Glu Gln Glu Leu Glu Glu Gln Glu Gln Glu Leu
            820                 825                 830
```

```
Glu Glu Gln Glu Gln Glu Leu Glu Glu Gln Glu Val Glu Gln Glu
            835                 840                 845
Gln Glu Val Glu Glu Gln Glu Gln Glu Gln Glu Gln Glu Leu Glu
        850                 855                 860
Glu Val Glu Glu Gln Glu Glu Gln Glu Gln Glu Gln Glu Gln Glu
865                 870                 875                 880
Leu Glu Glu Val Glu Glu Gln Glu Gln Glu Leu Glu Glu Val Glu
                885                 890                 895
Glu Gln Glu Gln Glu Leu Glu Glu Val Glu Glu Gln Glu Gln Gln
            900                 905                 910
Glu Leu Glu Glu Val Glu Glu Gln Glu Gln Gly Val Glu Gln Gln
        915                 920                 925
Glu Gln Glu Thr Val Glu Glu Pro Ile Ile Leu His Gly Ser Ser
    930                 935                 940
Glu Asp Glu Met Glu Val Asp Tyr Pro Val Val Ser Thr His Glu Gln
945                 950                 955                 960
Ile Ala Ser Ser Pro Pro Gly Asp Asn Thr Pro Asp Asp Pro Gln
                965                 970                 975
Pro Gly Pro Ser Arg Glu Tyr Arg Tyr Val Leu Arg Thr Ser Pro Pro
            980                 985                 990
His Arg Pro Gly Val Arg Met Arg Arg Val Pro Val Thr His Pro Lys
        995                 1000                1005
Lys Pro His Pro Arg Tyr Gln Gln Pro Pro Val Pro Tyr Arg Gln Ile
    1010                1015                1020
Asp Asp Cys Pro Ala Lys Ala Arg Pro Gln His Ile Phe Tyr Arg Arg
1025                1030                1035                1040
Phe Leu Gly Lys Asp Gly Arg Arg Asp Pro Lys Cys Gln Trp Lys Phe
                1045                1050                1055
Ala Val Ile Phe Trp Gly Asn Asp Pro Tyr Gly Leu Lys Lys Leu Ser
            1060                1065                1070
Gln Ala Phe Gln Phe Gly Gly Val Lys Ala Gly Pro Val Ser Cys Leu
        1075                1080                1085
Pro His Pro Gly Pro Asp Gln Ser Pro Ile Thr Tyr Cys Val Tyr Val
    1090                1095                1100
Tyr Cys Gln Asn Lys Asp Thr Ser Lys Lys Val Gln Met Ala Arg Leu
1105                1110                1115                1120
Ala Trp Glu Ala Ser His Pro Leu Ala Gly Asn Leu Gln Ser Ser Ile
                1125                1130                1135
Val Lys Phe Lys Lys Pro Leu Pro Leu Thr Gln Pro Gly Glu Asn Gln
            1140                1145                1150
Gly Pro Gly Asp Ser Pro Gln Glu Met Thr
        1155                1160
```

<210> SEQ ID NO 3
<211> LENGTH: 1926
<212> TYPE: DNA
<213> ORGANISM: Epstein-Barr virus

<400> SEQUENCE: 3

```
atgtctgacg aggggccagg tacaggacct ggaaatggcc taggagagaa gggagacaca    60
tctggaccag aaggctccgg cggcagtgga cctcaaagaa gaggggtgac taaccatgga   120
cgaggacggg gaagaggacg aggacgagga ggcggaagac caggagcccc gggcggctca   180
ggatcagggc caagacatag agatggtgtc cggagacccc aaaaacgtcc aagttgcatt   240
```

-continued

| | | | | | |
|---|---|---|---|---|---|
| ggctgcaaag | ggacccacgg | tggaacagga | gcaggagcag | gagcgggagg | ggcaggagca | 300 |
| ggaggggcag | gagcaggagg | agggcagga | gcaggaggag | gggcaggagg | ggcaggaggg | 360 |
| gcaggagggg | caggagcagg | aggaggggca | ggagcaggag | gaggggcagg | aggggcagga | 420 |
| gggcaggag | caggaggagg | ggcaggagca | ggaggagggg | caggaggggc | aggagcagga | 480 |
| ggaggggcag | gaggggcagg | agggcagga | gcaggaggag | gggcaggagc | aggaggaggg | 540 |
| gcaggagggg | caggagcagg | aggaggggca | ggaggggcag | gaggggcagg | agcaggagga | 600 |
| ggggcaggag | caggaggggc | aggaggggca | ggaggggcag | gagcaggagg | ggcaggagca | 660 |
| ggaggagggg | caggaggggc | aggaggggca | ggagcaggag | gggcaggagc | aggaggggca | 720 |
| ggagcaggag | gggcaggagc | aggaggggca | ggaggggcag | gagcaggagg | ggcaggaggg | 780 |
| gcaggagcag | gaggggcagg | aggggcagga | gcaggaggag | gggcaggagg | ggcaggagca | 840 |
| ggaggagggg | caggaggggc | aggagcagga | ggggcaggag | gggcaggagc | aggaggggca | 900 |
| ggaggggcag | gagcaggagg | ggcaggaggg | gcaggagcag | gaggagggc | aggagcagga | 960 |
| ggggcaggag | caggaggtgg | aggccggggt | cgaggaggca | gtggaggccg | gggtcgagga | 1020 |
| ggtagtggag | gccggggtcg | aggaggtagt | ggaggccgcc | ggggtagagg | acgtgaaaga | 1080 |
| gccaggggg | gaagtcgtga | aagagccagg | gggagaggtc | gtggacgtgg | agaaaagagg | 1140 |
| cccaggagtc | ccagtagtca | gtcatcatca | tccgggtctc | caccgcgcag | gcccctccca | 1200 |
| ggtagaaggc | cattttcca | ccctgtaggg | gaagccgatt | attttgaata | ccaccaagaa | 1260 |
| ggtggcccag | atggtgagcc | tgacgtgccc | ccgggagcga | tagagcaggg | ccccgcagat | 1320 |
| gacccaggag | aaggcccaag | cactggaccc | cggggtcagg | gtgatggagg | caggcgcaaa | 1380 |
| aaaggagggt | ggtttggaaa | gcatcgtggt | caaggaggtt | ccaacccgaa | atttgagaac | 1440 |
| attgcagaag | gtttaagagc | tctcctggct | aggagtcacg | tagaaaggac | taccgacgaa | 1500 |
| ggaacttggg | tcgccggtgt | gttcgtatat | ggaggtagta | agacctccct | ttacaaccta | 1560 |
| aggcgaggaa | ctgcccttgc | tattccacaa | tgtcgtctta | caccattgag | tcgtctcccc | 1620 |
| tttggaatgg | ccctggacc | cggcccacaa | cctggcccgc | taagggagtc | cattgtctgt | 1680 |
| tatttcatgg | tcttttaca | aactcatata | tttgctgagg | ttttgaagga | tgcgattaag | 1740 |
| gaccttgtta | tgacaaagcc | cgctcctacc | tgcaatatca | gggtgactgt | gtgcagcttt | 1800 |
| gacgatggag | tagatttgcc | tccctggttt | ccacctatgg | tggaaggggc | tgccgcggag | 1860 |
| ggtgatgacg | gagatgacgg | agatgaagga | ggtgatggag | atgagggtga | ggaagggcag | 1920 |
| gagtga | | | | | | 1926 |

<210> SEQ ID NO 4
<211> LENGTH: 641
<212> TYPE: PRT
<213> ORGANISM: Epstein-Barr virus

<400> SEQUENCE: 4

Met Ser Asp Glu Gly Pro Gly Thr Gly Pro Gly Asn Gly Leu Gly Glu
 1               5                  10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

-continued

```
Arg His Arg Asp Gly Val Arg Pro Gln Lys Arg Pro Ser Cys Ile
 65                  70                  75                  80

Gly Cys Lys Gly Thr His Gly Thr Gly Ala Gly Ala Gly Ala Gly
                 85                  90                  95

Gly Ala Gly Ala Gly Gly Ala Gly Gly Gly Ala Gly Ala Gly
                100                 105                 110

Gly Gly Ala Gly Gly Ala Gly Gly Ala Gly Gly Ala Gly Ala Gly
            115                 120                 125

Gly Ala Gly Ala Gly Gly Ala Gly Ala Gly Gly Ala Gly Ala
        130                 135                 140

Gly Gly Gly Ala Gly Ala Gly Gly Ala Gly Gly Ala Gly Ala Gly
145                 150                 155                 160

Gly Gly Ala Gly Gly Ala Gly Gly Ala Gly Gly Gly Ala Gly
                165                 170                 175

Ala Gly Gly Gly Ala Gly Gly Ala Gly Ala Gly Gly Ala Gly Gly
                180                 185                 190

Ala Gly Gly Ala Gly Ala Gly Gly Ala Gly Ala Gly Gly Ala Gly
                195                 200                 205

Gly Ala Gly Gly Ala Gly Ala Gly Gly Ala Gly Ala Gly Gly Ala
            210                 215                 220

Gly Gly Ala Gly Gly Ala Gly Ala Gly Gly Ala Gly Ala Gly Gly Ala
225                 230                 235                 240

Gly Ala Gly Gly Ala Gly Ala Gly Gly Ala Gly Gly Ala Gly Ala Gly
                245                 250                 255

Gly Ala Gly Gly Ala Gly Ala Gly Gly Ala Gly Gly Ala Gly Ala Gly
                260                 265                 270

Gly Gly Ala Gly Gly Ala Gly Ala Gly Gly Ala Gly Gly Ala Gly
            275                 280                 285

Ala Gly Gly Ala Gly Gly Ala Gly Ala Gly Gly Ala Gly Gly Ala Gly
                290                 295                 300

Ala Gly Gly Ala Gly Gly Ala Gly Ala Gly Gly Ala Gly Ala Gly
305                 310                 315                 320

Gly Ala Gly Ala Gly Gly Gly Gly Arg Gly Arg Gly Gly Ser Gly Gly
                325                 330                 335

Arg Gly Arg Gly Gly Ser Gly Gly Arg Gly Arg Gly Gly Ser Gly Gly
                340                 345                 350

Arg Arg Gly Arg Gly Arg Glu Arg Ala Arg Gly Gly Ser Arg Glu Arg
                355                 360                 365

Ala Arg Gly Arg Gly Arg Gly Arg Gly Glu Lys Arg Pro Arg Ser Pro
    370                 375                 380

Ser Ser Gln Ser Ser Ser Gly Ser Pro Pro Arg Arg Pro Pro Pro
385                 390                 395                 400

Gly Arg Arg Pro Phe Phe His Pro Val Gly Glu Ala Asp Tyr Phe Glu
                405                 410                 415

Tyr His Gln Glu Gly Gly Pro Asp Gly Glu Pro Asp Val Pro Pro Gly
            420                 425                 430

Ala Ile Glu Gln Gly Pro Ala Asp Asp Pro Gly Glu Gly Pro Ser Thr
            435                 440                 445

Gly Pro Arg Gly Gln Gly Asp Gly Gly Arg Arg Lys Lys Gly Gly Trp
    450                 455                 460

Phe Gly Lys His Arg Gly Gln Gly Gly Ser Asn Pro Lys Phe Glu Asn
465                 470                 475                 480
```

```
Ile Ala Glu Gly Leu Arg Ala Leu Leu Ala Arg Ser His Val Glu Arg
                485                 490                 495

Thr Thr Asp Glu Gly Thr Trp Val Ala Gly Val Phe Val Tyr Gly Gly
            500                 505                 510

Ser Lys Thr Ser Leu Tyr Asn Leu Arg Arg Gly Thr Ala Leu Ala Ile
        515                 520                 525

Pro Gln Cys Arg Leu Thr Pro Leu Ser Arg Leu Pro Phe Gly Met Ala
    530                 535                 540

Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Pro Thr Cys Asn
            580                 585                 590

Ile Arg Val Thr Val Cys Ser Phe Asp Asp Gly Val Asp Leu Pro Pro
            595                 600                 605

Trp Phe Pro Pro Met Val Glu Gly Ala Ala Glu Gly Asp Asp Gly
        610                 615                 620

Asp Asp Gly Asp Glu Gly Gly Asp Gly Asp Glu Gly Glu Glu Gly Gln
625                 630                 635                 640

Glu

<210> SEQ ID NO 5
<211> LENGTH: 28
<212> TYPE: DNA
<213> ORGANISM: Kaposi's sarcoma-associated herpesvirus

<400> SEQUENCE: 5
gagaattctt atggcgcccc cgggaatg                                          28

<210> SEQ ID NO 6
<211> LENGTH: 28
<212> TYPE: DNA
<213> ORGANISM: Kaposi's sarcoma-associated herpesvirus

<400> SEQUENCE: 6
gagatatccc tgtcatttcc tgtggaga                                          28
```